US010824921B2

(12) United States Patent
Bathiche et al.

(10) Patent No.: US 10,824,921 B2
(45) Date of Patent: Nov. 3, 2020

(54) POSITION CALIBRATION FOR INTELLIGENT ASSISTANT COMPUTING DEVICE

(71) Applicant: Microsoft Technology Licensing, LLC, Redmond, WA (US)

(72) Inventors: Steven Nabil Bathiche, Bellevue, WA (US); Flavio Protasio Ribeiro, Bellevue, WA (US); Vivek Pradeep, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 403 days.

(21) Appl. No.: 15/832,672

(22) Filed: Dec. 5, 2017

(65) Prior Publication Data

US 2018/0233145 A1    Aug. 16, 2018

Related U.S. Application Data

(60) Provisional application No. 62/459,020, filed on Feb. 14, 2017, provisional application No. 62/482,165, filed on Apr. 5, 2017.

(51) Int. Cl.
*G06T 7/70* (2017.01)
*G06N 20/00* (2019.01)
(Continued)

(52) U.S. Cl.
CPC ............ *G06K 9/726* (2013.01); *A61B 5/0205* (2013.01); *A61B 5/0507* (2013.01); *A61B 5/117* (2013.01);
(Continued)

(58) Field of Classification Search
CPC ...... G06K 9/726; G06K 9/00; G06K 9/00214; G06K 9/00255; G06K 9/00261;
(Continued)

(56) References Cited

U.S. PATENT DOCUMENTS 6,067,673 A    5/2000 Paese et al.
6,119,088 A    9/2000 Ciluffo
(Continued)

FOREIGN PATENT DOCUMENTS

EP    2947476 A1    11/2015
GB    2522922 A    8/2015
(Continued)

OTHER PUBLICATIONS

"Final Office Action Issued in U.S. Appl. No. 15/640,251", dated Apr. 2, 2019, 22 Pages.
(Continued)

*Primary Examiner* — Gregory J Toatley, Jr.
*Assistant Examiner* — Lynda Dinh
(74) *Attorney, Agent, or Firm* — Alleman Hall Creasman & Tuttle LLP

(57) ABSTRACT

A first intelligent assistant computing device configured to receive and respond to natural language inputs provided by human users syncs to a reference clock of a wireless computer network. The first intelligent assistant computing device receives a communication sent by a second intelligent assistant computing device indicating a signal emission time at which the second intelligent assistant computing device emitted a position calibration signal. The first intelligent assistant computing device records a signal detection time at which the position calibration signal was detected. Based on a difference between 1) the signal emission time and the signal detection time, and 2) a known propagation speed of the position calibration signal, a distance between the first and second intelligent assistant computing devices is calculated.

20 Claims, 15 Drawing Sheets

(51) Int. Cl.

| | |
|---|---|
| *G06F 21/32* | (2013.01) |
| *G10L 17/04* | (2013.01) |
| *G06K 9/00* | (2006.01) |
| *A61B 5/05* | (2006.01) |
| *G07C 9/32* | (2020.01) |
| *G01S 13/38* | (2006.01) |
| *G06K 9/72* | (2006.01) |
| *G06K 9/62* | (2006.01) |
| *G06F 3/16* | (2006.01) |
| *G10L 15/18* | (2013.01) |
| *G06T 7/292* | (2017.01) |
| *H04W 4/33* | (2018.01) |
| *H04W 4/029* | (2018.01) |
| *A61B 5/11* | (2006.01) |
| *A61B 5/117* | (2016.01) |
| *A61B 5/00* | (2006.01) |
| *G01S 5/28* | (2006.01) |
| *G06F 1/3206* | (2019.01) |
| *G06F 1/3231* | (2019.01) |
| *G06F 1/324* | (2019.01) |
| *G06F 3/01* | (2006.01) |
| *G06F 3/03* | (2006.01) |
| *G10L 17/08* | (2013.01) |
| *H04L 12/58* | (2006.01) |
| *H04L 29/08* | (2006.01) |
| *H04N 5/232* | (2006.01) |
| *H04N 7/18* | (2006.01) |
| *H04N 21/422* | (2011.01) |
| *H04N 21/442* | (2011.01) |
| *G07C 9/28* | (2020.01) |
| *G06F 40/35* | (2020.01) |
| *G06F 40/211* | (2020.01) |
| *G06T 7/73* | (2017.01) |
| *G06T 7/246* | (2017.01) |
| *G01S 5/18* | (2006.01) |
| *G06T 7/60* | (2017.01) |
| *G10L 15/22* | (2006.01) |
| *G10L 15/28* | (2013.01) |
| *H04R 1/40* | (2006.01) |
| *H04R 3/00* | (2006.01) |
| *H04N 5/33* | (2006.01) |
| *G10L 15/02* | (2006.01) |
| *G06N 5/02* | (2006.01) |
| *G06N 5/04* | (2006.01) |
| *G10L 15/06* | (2013.01) |
| *G10L 15/24* | (2013.01) |
| *G10L 15/26* | (2006.01) |
| *G10L 15/19* | (2013.01) |
| *G10L 15/08* | (2006.01) |
| *G10L 15/32* | (2013.01) |
| *G10L 25/51* | (2013.01) |
| *H04L 29/06* | (2006.01) |
| *A61B 5/0205* | (2006.01) |
| *G01S 13/72* | (2006.01) |
| *G06F 21/35* | (2013.01) |
| *G08B 13/14* | (2006.01) |
| *G06F 3/0482* | (2013.01) |
| *G06F 3/0484* | (2013.01) |
| *H04N 21/231* | (2011.01) |
| *G06F 3/0488* | (2013.01) |
| *G06F 16/70* | (2019.01) |
| *G01S 5/16* | (2006.01) |
| *G01S 11/14* | (2006.01) |
| *G01S 13/86* | (2006.01) |
| *G06N 3/04* | (2006.01) |
| *G08B 29/18* | (2006.01) |
| *G10L 17/00* | (2013.01) |
| *H04N 5/247* | (2006.01) |
| *G01S 13/88* | (2006.01) |

(52) U.S. Cl.
CPC ........... *A61B 5/1113* (2013.01); *A61B 5/7475* (2013.01); *G01S 5/18* (2013.01); *G01S 5/28* (2013.01); *G01S 13/726* (2013.01); *G06F 1/324* (2013.01); *G06F 1/3206* (2013.01); *G06F 1/3231* (2013.01); *G06F 3/011* (2013.01); *G06F 3/017* (2013.01); *G06F 3/0304* (2013.01); *G06F 3/0482* (2013.01); *G06F 3/04842* (2013.01); *G06F 3/167* (2013.01); *G06F 21/32* (2013.01); *G06F 21/35* (2013.01); *G06F 40/211* (2020.01); *G06F 40/35* (2020.01); *G06K 9/00* (2013.01); *G06K 9/00214* (2013.01); *G06K 9/00255* (2013.01); *G06K 9/00261* (2013.01); *G06K 9/00288* (2013.01); *G06K 9/00295* (2013.01); *G06K 9/00342* (2013.01); *G06K 9/00362* (2013.01); *G06K 9/00711* (2013.01); *G06K 9/00771* (2013.01); *G06K 9/00973* (2013.01); *G06K 9/6254* (2013.01); *G06K 9/6255* (2013.01); *G06K 9/6289* (2013.01); *G06K 9/6296* (2013.01); *G06N 5/025* (2013.01); *G06N 5/047* (2013.01); *G06N 20/00* (2019.01); *G06T 7/248* (2017.01); *G06T 7/292* (2017.01); *G06T 7/60* (2013.01); *G06T 7/70* (2017.01); *G06T 7/74* (2017.01); *G07C 9/28* (2020.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 17/04* (2013.01); *G10L 17/08* (2013.01); *G10L 25/51* (2013.01); *H04L 51/02* (2013.01); *H04L 63/102* (2013.01); *H04L 67/12* (2013.01); *H04L 67/22* (2013.01); *H04N 5/23219* (2013.01); *H04N 5/332* (2013.01); *H04N 7/181* (2013.01); *H04N 7/188* (2013.01); *H04N 21/231* (2013.01); *H04N 21/42203* (2013.01); *H04N 21/44218* (2013.01); *H04N 21/44222* (2013.01); *H04R 1/406* (2013.01); *H04R 3/005* (2013.01); *H04W 4/029* (2018.02); *H04W 4/33* (2018.02); *A61B 5/05* (2013.01); *A61B 5/1118* (2013.01); *G01S 5/16* (2013.01); *G01S 11/14* (2013.01); *G01S 13/38* (2013.01); *G01S 13/867* (2013.01); *G01S 13/888* (2013.01); *G06F 3/0488* (2013.01); *G06F 16/70* (2019.01); *G06F 2203/0381* (2013.01); *G06F 2221/2111* (2013.01); *G06K 2209/09* (2013.01); *G06N 3/0445* (2013.01); *G06T 2207/10016* (2013.01); *G06T 2207/10024* (2013.01); *G06T 2207/20101* (2013.01); *G06T 2207/30196* (2013.01); *G06T 2207/30201* (2013.01); *G06T 2207/30204* (2013.01); *G06T 2207/30232* (2013.01); *G07C 9/32* (2020.01); *G08B 29/186* (2013.01); *G10L 17/00* (2013.01); *G10L 2015/0635* (2013.01); *G10L 2015/088* (2013.01); *G10L 2015/223* (2013.01); *G10L 2015/225* (2013.01); *G10L*

*2015/228* (2013.01); *H04N 5/247* (2013.01); *Y02D 10/126* (2018.01); *Y02D 10/173* (2018.01)

(58) Field of Classification Search
CPC ........ G06K 9/00288; G06K 9/00295; G06K 9/00342; G06K 9/00362; G06K 9/00711; G06K 9/00771; G06K 9/00973; G06K 9/6254; G06K 9/6255; G06K 9/6289; G06K 9/6296; G06K 2209/09; G06T 7/292; G06T 7/74; G06T 7/248; G06T 7/70; G06T 7/60; G06T 2207/10016; G06T 2207/10024; G06T 2207/20101; G06T 2207/30196; G06T 2207/30201; G06T 2207/30204; G06T 2207/30232; H04W 4/33; H04W 4/029; G06N 20/00; G06N 5/025; G06N 5/047; G06N 3/0445; G06F 40/35; G06F 40/211; G06F 1/3206; G06F 1/3231; G06F 1/324; G06F 3/011; G06F 3/017; G06F 3/0304; G06F 3/0482; G06F 3/04842; G06F 3/167; G06F 3/0488; G06F 2203/0381; G06F 2221/2111; G06F 21/32; G06F 21/35; G06F 16/70; G07C 9/28; G07C 9/32; A61B 5/0205; A61B 5/0507; A61B 5/1113; A61B 5/117; A61B 5/7475; A61B 5/05; A61B 5/1118; G01S 5/18; G01S 5/28; G01S 5/16; G01S 11/14; G01S 13/726; G01S 13/38; G01S 13/867; G01S 13/888; G08B 13/1427; G08B 29/186; G10L 15/02; G10L 15/063; G10L 15/08; G10L 15/18; G10L 15/1815; G10L 15/1822; G10L 15/19; G10L 15/22; G10L 15/24; G10L 15/26; G10L 15/28; G10L 15/32; G10L 17/00; G10L 17/04; G10L 17/08; G10L 25/51; G10L 2015/0635; G10L 2015/088; G10L 2015/223; G10L 2015/225; G10L 2015/228; H04L 51/02; H04L 63/102; H04L 67/12; H04L 67/22; H04N 5/23219; H04N 5/332; H04N 5/247; H04N 7/181; H04N 7/188; H04N 21/231; H04N 7/42203; H04N 7/44218; H04N 7/44222; H04R 1/406; H04R 3/005; Y02D 10/173; Y02D 10/126

See application file for complete search history.

(56) References Cited

U.S. PATENT DOCUMENTS

| | | |
|---|---|---|
| 6,332,122 B1 | 12/2001 | Ortega et al. |
| 6,442,524 B1 | 8/2002 | Ecker et al. |
| 6,477,500 B2 | 11/2002 | Maes |
| 6,496,799 B1 | 12/2002 | Pickering |
| 6,574,601 B1 | 6/2003 | Brown et al. |
| 6,727,925 B1 | 4/2004 | Bourdelais |
| 6,728,679 B1 | 4/2004 | Strubbe et al. |
| 6,816,730 B2 | 11/2004 | Davies et al. |
| 6,873,953 B1 | 3/2005 | Lennig |
| 7,019,749 B2 | 3/2006 | Guo et al. |
| 7,050,110 B1 | 5/2006 | Lienhart et al. |
| 7,330,566 B2 | 2/2008 | Cutler |
| 7,475,010 B2 | 1/2009 | Chao |
| 7,610,365 B1 | 10/2009 | Kraft et al. |
| 7,716,056 B2 | 5/2010 | Weng et al. |
| 7,803,050 B2 | 9/2010 | Mao et al. |
| 8,139,945 B1 | 3/2012 | Amir et al. |
| 8,165,087 B2 | 4/2012 | Panabaker |
| 8,170,875 B2 | 5/2012 | Hetherington et al. |
| 8,213,689 B2 | 7/2012 | Yagnik et al. |
| 8,265,252 B2 | 9/2012 | Ducheneaut et al. |
| 8,326,627 B2 | 12/2012 | Kennewick et al. |
| 8,340,975 B1 | 12/2012 | Rosenberger |
| 8,374,879 B2 | 2/2013 | Falcon et al. |
| 8,453,402 B2 | 6/2013 | Huang |
| 8,457,959 B2 | 6/2013 | Kaiser |
| 8,543,402 B1 | 9/2013 | Ma |
| 8,639,762 B2 | 1/2014 | Rasmussen et al. |
| 8,644,842 B2 | 2/2014 | Arrasvuori et al. |
| 8,712,758 B2 | 4/2014 | Crouch et al. |
| 8,752,145 B1 | 6/2014 | Dotan et al. |
| 8,762,150 B2 | 6/2014 | Edgington et al. |
| 8,762,156 B2 | 6/2014 | Chen |
| 8,779,965 B2 | 7/2014 | Sentelle et al. |
| 8,805,691 B2 | 8/2014 | Genly |
| 8,861,924 B2 | 10/2014 | Meads et al. |
| 8,862,156 B2 | 10/2014 | Bell et al. |
| 8,885,882 B1 | 11/2014 | Reale et al. |
| 8,903,128 B2 | 12/2014 | Shet et al. |
| 8,913,103 B1 | 12/2014 | Sargin et al. |
| 8,942,986 B2 | 1/2015 | Cheyer et al. |
| 8,949,359 B2 | 2/2015 | Rasmussen et al. |
| 9,037,601 B2 | 5/2015 | Palay |
| 9,070,366 B1 | 6/2015 | Mathias et al. |
| 9,085,303 B2 | 7/2015 | Wolverton et al. |
| 9,119,512 B2 | 9/2015 | Martins, Jr. et al. |
| 9,123,330 B1 | 9/2015 | Sharifi et al. |
| 9,171,542 B2 | 10/2015 | Gandrabur et al. |
| 9,230,544 B2 | 1/2016 | Kwon et al. |
| 9,268,406 B2 | 2/2016 | Geisner et al. |
| 9,300,925 B1 | 3/2016 | Zhang |
| 9,307,355 B2 | 4/2016 | Nehrenz et al. |
| 9,311,932 B2 | 4/2016 | Carter |
| 9,318,105 B1 | 4/2016 | Khosla |
| 9,348,990 B2 | 5/2016 | Chuaprasert et al. |
| 9,368,114 B2 | 6/2016 | Larson et al. |
| 9,378,740 B1 | 6/2016 | Rosen et al. |
| 9,380,177 B1 | 6/2016 | Rao et al. |
| 9,389,681 B2 | 7/2016 | Sankar et al. |
| 9,412,392 B2 | 8/2016 | Lindahl |
| 9,424,840 B1 | 8/2016 | Hart et al. |
| 9,466,286 B1 | 10/2016 | Hart et al. |
| 9,495,331 B2 | 11/2016 | Govrin et al. |
| 9,495,613 B2 | 11/2016 | Holz et al. |
| 9,507,977 B1 | 11/2016 | Mor et al. |
| 9,508,341 B1 | 11/2016 | Parlikar et al. |
| 9,514,227 B1 | 12/2016 | Garrett et al. |
| 9,558,749 B1 | 1/2017 | Secker-Walker et al. |
| 9,576,574 B2 | 2/2017 | van Os |
| 9,622,059 B2 | 4/2017 | Bouzid et al. |
| 9,626,352 B2 | 4/2017 | Allen et al. |
| 9,633,652 B2 | 4/2017 | Kurniawati et al. |
| 9,669,296 B1 | 6/2017 | Hibbert et al. |
| 9,749,583 B1 | 8/2017 | Fineberg et al. |
| 9,761,055 B2 | 9/2017 | Miller |
| 9,767,616 B2 | 9/2017 | Miller |
| 9,842,299 B2 | 12/2017 | Stolarz et al. |
| 9,898,250 B1 | 2/2018 | Williams et al. |
| 9,965,247 B2 | 5/2018 | Jarvis et al. |
| 10,178,301 B1 | 1/2019 | Welbourne et al. |
| 10,276,149 B1 | 4/2019 | Liang et al. |
| 10,482,885 B1 | 11/2019 | Moniz |
| 10,599,390 B1 | 3/2020 | Brahmbhatt et al. |
| 2003/0103647 A1 | 6/2003 | Rui et al. |
| 2003/0131064 A1 | 7/2003 | Bell et al. |
| 2005/0182627 A1 | 8/2005 | Tanaka et al. |
| 2005/0216264 A1 | 9/2005 | Attwater et al. |
| 2005/0225427 A1 | 10/2005 | Bell et al. |
| 2005/0285774 A1 | 12/2005 | Wittenberg et al. |
| 2006/0028552 A1 | 2/2006 | Aggarwal et al. |
| 2006/0067536 A1* | 3/2006 | Culbert ............ H04S 1/007 381/58 |
| 2007/0024487 A1 | 2/2007 | Zemany et al. |
| 2007/0100480 A1 | 5/2007 | Sinclair et al. |
| 2007/0152157 A1 | 7/2007 | Page |
| 2007/0198245 A1 | 8/2007 | Kamatani et al. |
| 2007/0271086 A1 | 11/2007 | Peters et al. |
| 2008/0030345 A1 | 2/2008 | Austin et al. |
| 2008/0071547 A1 | 3/2008 | Prieto et al. |

(56) References Cited

U.S. PATENT DOCUMENTS

| | | |
|---|---|---|
| 2008/0077015 A1 | 3/2008 | Boric-lubecke et al. |
| 2008/0195387 A1 | 8/2008 | Zigel et al. |
| 2008/0288251 A1 | 11/2008 | Cooper et al. |
| 2009/0066690 A1 | 3/2009 | Harrison |
| 2009/0303342 A1 | 12/2009 | Corcoran et al. |
| 2009/0319269 A1 | 12/2009 | Aronowitz |
| 2010/0073363 A1 | 3/2010 | Densham et al. |
| 2010/0100851 A1 | 4/2010 | Clark et al. |
| 2010/0179813 A1 | 7/2010 | Summerfield et al. |
| 2010/0195906 A1 | 8/2010 | Uliyar et al. |
| 2011/0010170 A1 | 1/2011 | Burns et al. |
| 2011/0119060 A1 | 5/2011 | Aronowitz |
| 2011/0184735 A1 | 7/2011 | Flaks et al. |
| 2011/0216090 A1 | 9/2011 | Woo et al. |
| 2011/0219339 A1 | 9/2011 | Densham |
| 2011/0298967 A1 | 12/2011 | Clavin et al. |
| 2011/0302535 A1 | 12/2011 | Clerc et al. |
| 2012/0026335 A1 | 2/2012 | Brown et al. |
| 2012/0253791 A1 | 10/2012 | Heck et al. |
| 2012/0265535 A1 | 10/2012 | Bryant-rich et al. |
| 2012/0268604 A1 | 10/2012 | Tree |
| 2013/0110519 A1 | 5/2013 | Cheyer et al. |
| 2013/0117377 A1 | 5/2013 | Miller |
| 2013/0144616 A1 | 6/2013 | Bangalore |
| 2013/0212501 A1 | 8/2013 | Anderson et al. |
| 2013/0253936 A1 | 9/2013 | Harvey |
| 2013/0259456 A1 | 10/2013 | Viswanathan |
| 2013/0304479 A1 | 11/2013 | Teller et al. |
| 2013/0342568 A1 | 12/2013 | Ambrus et al. |
| 2014/0033071 A1 | 1/2014 | Gruber et al. |
| 2014/0067679 A1 | 3/2014 | O'reilly et al. |
| 2014/0100997 A1 | 4/2014 | Mayerle et al. |
| 2014/0156276 A1 | 6/2014 | Nakano et al. |
| 2014/0160290 A1 | 6/2014 | Wu |
| 2014/0180629 A1 | 6/2014 | Dokmanic et al. |
| 2014/0214421 A1 | 7/2014 | Shriberg et al. |
| 2014/0214429 A1 | 7/2014 | Pantel |
| 2014/0222422 A1 | 8/2014 | Sarikaya et al. |
| 2014/0244263 A1 | 8/2014 | Pontual et al. |
| 2014/0272821 A1 | 9/2014 | Pitschel et al. |
| 2014/0330569 A1 | 11/2014 | Kolavennu et al. |
| 2014/0341440 A1 | 11/2014 | Walch |
| 2014/0365226 A1* | 12/2014 | Sinha ............ H04M 1/72519 704/275 |
| 2015/0016642 A1 | 1/2015 | Walsh et al. |
| 2015/0019714 A1 | 1/2015 | Shaashua et al. |
| 2015/0025887 A1 | 1/2015 | Sidi et al. |
| 2015/0032254 A1 | 1/2015 | Ishiguro |
| 2015/0032456 A1 | 1/2015 | Wait |
| 2015/0035976 A1 | 2/2015 | Mayuzumi |
| 2015/0102996 A1 | 4/2015 | Yim et al. |
| 2015/0134547 A1 | 5/2015 | Oikonomidis |
| 2015/0138332 A1 | 5/2015 | Cheng et al. |
| 2015/0149179 A1 | 5/2015 | Korbecki |
| 2015/0149182 A1 | 5/2015 | Kalns et al. |
| 2015/0162000 A1 | 6/2015 | Di censo et al. |
| 2015/0172285 A1 | 6/2015 | Lo et al. |
| 2015/0195666 A1* | 7/2015 | Massey ............... G01S 11/14 381/59 |
| 2015/0220244 A1 | 8/2015 | Vats et al. |
| 2015/0249664 A1 | 9/2015 | Talhami et al. |
| 2015/0279368 A1 | 10/2015 | Contolini et al. |
| 2015/0340033 A1 | 11/2015 | Di fabbrizio et al. |
| 2015/0347114 A1 | 12/2015 | Yoon |
| 2015/0371639 A1 | 12/2015 | Foerster et al. |
| 2015/0382047 A1 | 12/2015 | Van os et al. |
| 2016/0019889 A1 | 1/2016 | Alvarez guevara et al. |
| 2016/0063989 A1 | 3/2016 | Deleeuw |
| 2016/0086018 A1 | 3/2016 | Lemoff |
| 2016/0088043 A1 | 3/2016 | Jiang et al. |
| 2016/0092732 A1 | 3/2016 | Black |
| 2016/0138247 A1 | 5/2016 | Conway et al. |
| 2016/0148417 A1 | 5/2016 | Kim et al. |
| 2016/0155443 A1 | 6/2016 | Khan et al. |
| 2016/0171289 A1* | 6/2016 | Lee ..................... G06F 3/011 382/118 |
| 2016/0173293 A1 | 6/2016 | Kennedy |
| 2016/0179831 A1 | 6/2016 | Gruber et al. |
| 2016/0187961 A1 | 6/2016 | Elibol et al. |
| 2016/0203002 A1 | 7/2016 | Kannan et al. |
| 2016/0210411 A1 | 7/2016 | Mentis |
| 2016/0217783 A1 | 7/2016 | Konuma et al. |
| 2016/0225373 A1 | 8/2016 | Casado et al. |
| 2016/0234595 A1 | 8/2016 | Goran et al. |
| 2016/0234616 A1 | 8/2016 | Gateau |
| 2016/0259623 A1* | 9/2016 | Sumner ................ H04L 67/10 |
| 2016/0283185 A1 | 9/2016 | Mclaren et al. |
| 2016/0342702 A1 | 11/2016 | Barve et al. |
| 2016/0358598 A1 | 12/2016 | Williams et al. |
| 2016/0360336 A1 | 12/2016 | Gross et al. |
| 2016/0380929 A1 | 12/2016 | Katis et al. |
| 2017/0013409 A1 | 1/2017 | Cerchio et al. |
| 2017/0025124 A1 | 1/2017 | Mixter et al. |
| 2017/0032021 A1 | 2/2017 | Watanachote |
| 2017/0032787 A1 | 2/2017 | Dayal |
| 2017/0039423 A1 | 2/2017 | Cork et al. |
| 2017/0039602 A1 | 2/2017 | Shi-nash et al. |
| 2017/0068423 A1 | 3/2017 | Napolitano et al. |
| 2017/0078573 A1 | 3/2017 | Chen et al. |
| 2017/0133011 A1 | 5/2017 | Chen et al. |
| 2017/0140760 A1 | 5/2017 | Sachdev |
| 2017/0169476 A1 | 6/2017 | Nomula et al. |
| 2017/0185375 A1 | 6/2017 | Martel et al. |
| 2017/0186290 A1 | 6/2017 | Li et al. |
| 2017/0194000 A1 | 7/2017 | Itani et al. |
| 2017/0206900 A1 | 7/2017 | Lee et al. |
| 2017/0230705 A1 | 8/2017 | Pardue et al. |
| 2017/0236512 A1 | 8/2017 | Williams et al. |
| 2017/0242651 A1 | 8/2017 | Lang et al. |
| 2017/0249309 A1 | 8/2017 | Sarikaya |
| 2017/0255450 A1 | 9/2017 | Mullins et al. |
| 2017/0262472 A1 | 9/2017 | Goldenberg |
| 2017/0269975 A1 | 9/2017 | Wood et al. |
| 2017/0278480 A1 | 9/2017 | Sung et al. |
| 2017/0286530 A1 | 10/2017 | Paruchuri et al. |
| 2017/0287490 A1 | 10/2017 | Biswal et al. |
| 2017/0315208 A1 | 11/2017 | Sadr |
| 2017/0322939 A1 | 11/2017 | Byron et al. |
| 2017/0351749 A1 | 12/2017 | Quirk et al. |
| 2017/0357637 A1* | 12/2017 | Nell ................... H04L 12/2823 |
| 2017/0359666 A1 | 12/2017 | Lyren et al. |
| 2018/0009118 A1 | 1/2018 | Yamaga et al. |
| 2018/0047394 A1 | 2/2018 | Tian et al. |
| 2018/0048768 A1 | 2/2018 | Spittle et al. |
| 2018/0074785 A1 | 3/2018 | Ohmura |
| 2018/0090143 A1* | 3/2018 | Saddler ................. G06F 3/167 |
| 2018/0091782 A1 | 3/2018 | Bashkin |
| 2018/0096696 A1 | 4/2018 | Mixter |
| 2018/0158454 A1 | 6/2018 | Campbell et al. |
| 2018/0199123 A1 | 7/2018 | Rao et al. |
| 2018/0218080 A1 | 8/2018 | Krishnamurthy et al. |
| 2018/0231653 A1 | 8/2018 | Pradeep et al. |
| 2018/0232201 A1 | 8/2018 | Holtmann |
| 2018/0232563 A1 | 8/2018 | Albadawi et al. |
| 2018/0232571 A1 | 8/2018 | Bathiche et al. |
| 2018/0232608 A1 | 8/2018 | Pradeep et al. |
| 2018/0232645 A1 | 8/2018 | Finkelstein et al. |
| 2018/0232662 A1 | 8/2018 | Solomon et al. |
| 2018/0232902 A1 | 8/2018 | Albadawi et al. |
| 2018/0233132 A1 | 8/2018 | Herold et al. |
| 2018/0233139 A1 | 8/2018 | Finkelstein et al. |
| 2018/0233140 A1 | 8/2018 | Koishida et al. |
| 2018/0233141 A1 | 8/2018 | Solomon et al. |
| 2018/0233142 A1 | 8/2018 | Koishida et al. |
| 2018/0260680 A1 | 9/2018 | Finkelstein et al. |
| 2018/0293221 A1 | 10/2018 | Finkelstein et al. |
| 2018/0314689 A1 | 11/2018 | Wang et al. |
| 2018/0333862 A1 | 11/2018 | Hayashi |
| 2019/0057703 A1 | 2/2019 | Zeinstra |
| 2020/0012906 A1 | 1/2020 | Albadawi et al. |

(56) References Cited

U.S. PATENT DOCUMENTS

2020/0042839 A1 2/2020 Herold et al.
2020/0104653 A1 4/2020 Solomon et al.

FOREIGN PATENT DOCUMENTS

| KR | 1020070016280 A | 2/2007 |
|---|---|---|
| WO | 2007018523 A2 | 2/2007 |
| WO | 2010104772 A1 | 9/2010 |
| WO | 2013061268 A2 | 5/2013 |
| WO | 2015012449 A1 | 1/2015 |
| WO | 2016114922 A1 | 7/2016 |
| WO | 2016162678 A1 | 10/2016 |
| WO | 2016205419 A1 | 12/2016 |

OTHER PUBLICATIONS

Miro, et al., "Speaker Diarization: A review of Recent Research", In the Proceedings of IEEE Transactions on Audio, Speech and Language Processing, vol. 20, Issue 2, Feb. 1, 2012, 15 Pages.
Moattar, et al., "A Review on Speaker Diarization Systems and Approaches", In the Publication of Speech Communication, vol. 54, Issue 10, Dec. 12, 2010, 39 Pages.
"International Search Report & Written Opinion for PCT Patent Application No. PCT/US2018/062384", dated Feb. 15, 2019, 12 Pages.
Yu, et al., "Smart Meeting Systems: A Survey of State of the Art and Open Issues", In the Proceedings of ACM Computing Surveys, vol. 42, No. 2, Mar. 5, 2010, 20 Pages.
"Non Provisional Application Filed in U.S. Appl. No. 15/885,518", filed Jan. 31, 2018, 40 Pages.
"Non-Final Office Action Issued in U.S. Appl. No. 15/646,871", dated Sep. 3, 2019, 23 Pages.
"Final Office Action Issued in U.S. Appl. No. 15/657,822", dated Aug. 22, 2019, 22 Pages.
"Final Office Action Issued in U.S. Appl. No. 15/832,656", dated Aug. 23, 2019, 10 Pages.
Constine, Jose, "Instagram launches selfie filters, copying the last big Snapchat feature", Retrieved From. https://techcrunch.com/2017/05/16/instagram-face-filters/, May 16, 2017, 8 Pages.
"International Search Report and Written Opinion Issued in PCT Application No. PCT/US2019/022836", dated Jun. 24, 2019, 15 Pages.
"International Search Report and Written Opinion Issued in PCT Application No. PCT/US2019/029558", dated Jun. 28, 2019, 10 Pages.
"Sara: the Socially Aware Robot Assistant", Retrieved from: https://web.archive.org/web/20160707141922/http:/articulab.hcii.cs.cmu.edu:80/projects/sara/, Jul. 7, 2017, 10 Pages.
Arsikere, et al., "Computationally-efficient Endpointing Features for Natural Spoken Interaction with Personal-Assistant Systems", In Proceedings of IEEE International Conference on Acoustics, Speech and Signal Processing, May 4, 2014, pp. 3241-3245.
Ferrer, et al., "Is the Speaker Done Yet? Faster and More Accurate End-of-Utterance Detection using Prosody", In the proceedings of Seventh International Conference on Spoken Language Processing, Sep. 16, 2002, pp. 2061-2064.
Lacharite, Noelle, "Updated: Alexa Skills Kit Fact Template: Step-by-Step Guide to Build a Fact Skill", Retrieved from: https://developer.amazon.com/blogs/post/Tx3DVGG0K0TPUGQ/New-Alexa-Skills-Kit-Template:-Step-by-Step-Guide-to-Build-a-Fact-Skill, Mar. 29, 2016, 33 Pages.
"International Search Report and Written Opinion Issued in PCT Application No. PCT/US2018/017140", dated May 18, 2018, 12 Pages.
"International Search Report and Written Opinion Issued in PCT Application No. PCT/US2018/017514", dated May 17, 2018, 12 Pages.
Porcheron, et al., "Do Animals Have Accents?": Talking with Agents in Multi-Party Conversation, In Proceedings of 20th ACM Conference on Computer-Supported cooperative Work and Social Computing, Feb. 25, 2017, 14 Pages.
Xiang, Li, "Improving Knowledge Base Population With Information Extraction", A Thesis Submitted in Partial fullfillment of the Requirements of the University of New York for the Degree of Doctor of Philosophy, May 2016, 131 Pages.
Yun-Nung, Chen, "Unsupervised Learning and Modeling of Knowledge and Intent for Spoken Dialogue Systems", In Proceedings of the 53rd Annual Meeting of the Association for Computational Linguistics, Jul. 28, 2015, 8 Pages.
Zhang, et al., "A Joint Model of Intent Determination and Slot Filling for Spoken Language Understanding", In Proceedings of the Twenty-Fifth International Joint Conference on Artificial Intelligence, Jul. 9, 2016, pp. 2993-2999.
"Notice of Allowance Issued in U.S. Appl. No. 16/573,677", dated Nov. 6, 2019, 9 Pages.
"Non Final Office Action Issued in U.S. Appl. No. 15/832,656", dated Jan. 6, 2020, 9 Pages.
"Non Final Office Action Issued in U.S. Appl. No. 15/657,822", dated Feb. 6, 2020, 25 Pages.
"Final Office Action Issued in U.S. Appl. No. 15/646,871", dated Jan. 21, 2020, 23 Pages.
"Final Office Action Issued in U.S. Appl. No. 15/640,251", dated Jan. 30, 2020, 21 Pages.
"Non Final Office Action Issued in U.S. Appl. No. 16/005,470", dated Feb. 24, 2020, 11 Pages.
"Non Final Office Action Issued in U.S. Appl. No. 15/640,251", dated Sep. 12, 2019, 21 Pages.
Staff, Appleinsider, "Amazon Alexa's 'Follow-Up Mode' Enables Successive Requests Without Trigger Word", Retrieved From https://appleinsider.com/articles/18/03/09/amazon-alexas-follow-up-mode-enables-successive-requests-without-trigger-word, Mar. 9, 2018, 7 Pages.
"Multiple Agents (Each Trained for Different Domain) for One Chat Bot?", Retrieved From https://discuss.api.ai/t/multiple-agents-each-trained-for-different-domain-for-one-chat-bot/1002, Jul. 1, 2016, 1 Page.
"Train the Natural Language Processing Classifiers", Retrieved From https://www.mindmeld.com/docs/train_the_natural_language_processing_classifiers.html, Retrieved on: May 2, 2017, 10 Pages.
"Using Multiple Alexa Devices", Retrieved From https://www.amazon.com/gp/help/customer/display.html?nodeId=202013740, Apr. 24, 2017, 2 Pages.
"Application Filed in U.S. Appl. No. 15/395,961", filed Dec. 30, 2016, 79 Pages.
Ballan, et al., "Event Detection and Recognition for Semantic Annotation of Video", In Journal of Multimedia Tools and Applications, vol. 51, Issue 1, Nov. 10, 2010, pp. 279-302.
Beltagy, et al., "Improved Semantic Parsers for If-Then Statements", In Proceedings of the 54th Annual Meeting of the Association for Computational Linguistics, vol. 1, Aug. 7, 2016, pp. 726-736.
Boakye, et al., "Overlapped Speech Detection for Improved Speaker Diarization in Multiparty Meetings", In Proceedings of IEEE International Conference on Acoustics, Speech and Signal Processing, Mar. 31, 2008, 4 Pages.
Cho, et al., "A Multi-Sensor Fusion System for Moving Object Detection and Tracking in Urban Driving Environments", In IEEE International Conference on Robotics & Automation, May 31, 2014, 8 Pages.
Fossard, et al., Between Anaphora and Deixis . . . The Resolution of the Demonstrative Noun Phrase "that N", In Journal of Language and Cognitive Processes, vol. 27, Issue 9, Nov. 2, 2011, 3 Pages.
Gebhart, Andrew, "How to bring Alexa into every room of your home", Retrieved From https://www.cnet.com/how-to/how-to-install-alexa-in-every-room-of-your-home/, Feb. 2, 2017, 7 Pages.
Goncalves, et al., "Assessing Users' Emotion at Interaction Lime: A Multimodal Approach With Multiple Sensors", In Proceedings of Soft Computing, vol. 21, Issue 18, Sep. 1, 2017, 8 Pages.
Goswami, et al., "A Reviewon Low Light Image Enhancement Using Image Processing Technique", In International Journal of Technical Research, vol. 5, Issue 1, Mar. 2016, pp. 60-62.

(56) References Cited

OTHER PUBLICATIONS

He, et al., "Sensor Scheduling for Target Tracking: A Monte Carlo sampling approach", In Journal of Digital Signal Processing, vol. 16, Issue 5, Sep. 2006, pp. 533-545.

Huijbregts, et al., "Speech Overlap Detection in a Two-Pass Speaker Diarization System", In Proceedings of 10th Annual Conference of the International Speech Communication, Sep. 6, 2009, pp. 1063-1066.

Kabadjov, Mijail Alexandrov., "A Comprehensive Evaluation of Anaphora Resolution and Discourse—new Classification", In thesis of University of Essex, May 2007, 266 Pages.

Kang, et al., "Detection and Tracking of Moving Objects from Overlapping EO and IR Sensors", In Conference on Computer Vision and Pattern Recognition Workshop, Jun. 27, 2004, 6 Pages.

Kozhaya, Joe, "10 Steps to Train an Effective Chatbot and its Machine Learning Models", Retrieved From https://developer.ibm.com/dwblog/2016/10-steps-train-chat-bot-chatbot-machine-learning/, Dec. 12, 2016, 7 Pages.

Li et al., "A Multiple-Camera System Calibration Toolbox Using a Feature Descriptor-based Calibration Pattern", In Proceedings of IEEE International Conference on Intelligent Robots and Systems, Nov. 3, 2013, pp. 1301-1307.

Liu, et al., "Reliable Multiple Object Tracking under Heavy Occlusions", In Proceedings on Intelligence Information Processing and Trusted Computing (IPTC), International Symposium, Oct. 28, 2010, 3 Pages.

Mengusoglu, Erhan, "Confidence Measures for Speech/Speaker Recognition and Applications on Turkish LVCSR", Retrieved From https://web.archive.org/web/20040619044603/http://www.tcts.fpms.ac.be/publications/phds/mengusoglu/thesis_mengus.pdf, Apr. 20, 2004, 143 Pages.

Verma et al., "Face Detection and Tracking in a Video by Propagating Detection Probabilities", In Proceedings of IEEE Transactions on Pattern Analysis and Machine Intelligence, vol. 25, Issue 10, Oct. 1, 2003, pp. 1215-1228.

M. K., et al., "Ambiguities in Natural Language Processing", In International Journal of Innovative Research in Computer and Communication Engineering, vol. 2, Special Issue 5, Oct. 2014, pp. 392-394.

Pan, et al., "Robust Occlusion Handling in Object Tracking", In IEEE Conference on Computer Vision and Pattern Recognition, Jun. 17, 2007, 8 Pages.

Panzarino, Matthew, "Here's an Actual 3D Indoor Map of a Room Captured With Google's Project Tango Phone", Retrieved From https://techcrunch.com/2014/02/21/heres-an-actual-3d-indoor-map-of-a-room-captured-with-googles-project-tango-phone/, Feb. 21, 2014, 6 Pages.

"International Search Report and Written Opinion Issued in PCT Application No. PCT/US2018/017139", dated May 8, 2018, 13 Pages.

"International Search Report and Written Opinion Issued in PCT Application No. PCT/US2018/017506", dated May 4, 2018, 13 Pages.

"International Search Report and Written Opinion Issued in PCT Application No. PCT/US2018/017508", dated May 8, 2018, 13 Pages.

"International Search Report and Written Opinion Issued in PCT Application No. PCT/US2018/017509", dated May 11, 2018, 11 Pages.

"International Search Report and Written Opinion Issued in PCT Application No. PCT/US2018/017510", dated Apr. 20, 2018, 14 Pages.

"International Search Report and Written Opinion Issued in PCT Application No. PCT/US2018/017511", dated May 17, 2018, 12 Pages.

"International Search Report and Written Opinion Issued in PCT Application No. PCT/US2018/017512", dated May 4, 2018, 15 Pages.

"International Search Report and Written Opinion Issued in PCT Application No. PCT/US2018/017513", dated Apr. 12, 2018, 15 Pages.

"International Search Report and Written Opinion Issued in PCT Application No. PCT/US2018/017515", dated May 9, 2018, 12 Pages.

"International Search Report and Written Opinion Issued in PCT Application No. PCT/US2018/017517", dated May 11, 2018, 12 Pages.

Pullen, John Patrick., "Amazon Echo Tip: How to Add Multiple Users ! Time", Retrieved From http://time.com/4668359/amazon-echo-alexa-multiple-accounts/, Feb. 13, 2017, 3 Pages.

Quirk, et al., "Language to Code: Learning Semantic Parsers for If-This-Then-That Recipes", In Proceedings of the 53rd Annual Meeting of the Association for Computational Linguistics, Jul. 26, 2015, pp. 878-888.

Rizwan, et al., "Local Enhancement for Robust Face Detection in Poor SNR Images", In International Journal of Computer Science and Network Security, vol. 9, Issue 6, Jun. 2009, pp. 93-96.

Sinha, et al., "An Analysis Engine for Dependable Elicitation on Natural Language Use Case Description and its Application to Industrial Use Cases", In IBM Research Report, RC242712, Dec. 18, 2008, 12 Pages.

Toutanova, et al., "Compositional Learning of Embeddings for Relation Paths in Knowledge Bases and Text", In Proceedings of the 54th Annual Meeting of the Association for Computational Linguistics, Aug. 7, 2016, pp. 1434-1444.

Wagner, Martin, "Tracking with Multiple Sensors", Faculty of Computer Science at the Technical University of Munich, Sep. 12, 2004, 202 Pages.

Wheeler, et al., "Face Recognition at a Distance", In Publication of Springer, Jan. 2011, pp. 353-381.

Yamamoto, S, et al., "Algorithm Optimizations for Low-Complexity Eye Tracking", In Proceedings of IEEE International Conference on Systems, Man, and Cybernetics, Oct. 2009, pp. 18-22.

Kalal, et al., "Face-TLD: Tracking-Learning-Detection Applied to Faces", In Proceedings of 17th IEEE International Conference on Image Processing, Sep. 26, 2010, pp. 3789-3792.

Zotkin, et al., "Joint Audio-Visual Tracking Using Particle Filters", In EURASIP Journal on Applied Signal Processing, vol. 2002, Issue 1, Jan. 2002, pp. 1154-1164.

"Final Office Action Issued in U.S. Appl. No. 15/646,871", dated Apr. 19, 2019, 22 Pages.

"Non Final Office Action Issued in U.S. Appl. No. 15/682,407", dated Jun. 26, 2019, 15 Pages.

"Non Final Office Action Issued in U.S. Appl. No. 15/682,425", dated May 6, 2019, 12 Pages.

"Non Final Office Action Issued in U.S. Appl. No. 15/636,422", dated Sep. 4, 2018, 11 Pages.

"Non Final Office Action Issued in U.S. Appl. No. 15/640,251", dated Oct. 15, 2018, 22 Pages.

"Non Final Office Action Issued in U.S. Appl. No. 15/646,871", dated Dec. 19, 2018, 22 Pages.

"Non Final Office Action Issued in U.S. Appl. No. 15/656,994", dated Jan. 22, 2019, 8 Pages.

"Non Final Office Action Issued in U.S. Appl. No. 15/657,031", dated Oct. 5, 2018, 16 Pages.

"Non-Final Office Action Issued in U.S. Appl. No. 15/657,822", dated Feb. 21, 2019, 25 Pages.

"Non Final Office Action Issued in U.S. Appl. No. 15/832,656", dated Feb. 7, 2019, 8 Pages.

"Non Final Office Action Issued in U.S. Appl. No. 15/640,113", dated May 14, 2020, 13 Pages.

"Non Final Office Action Issued in U.S. Appl. No. 15/640,201", dated May 27, 2020, 11 Pages.

"Notice of Allowance Issued in U.S. Appl. No. 15/832,656", dated Apr. 22, 2020, 8 Pages.

"Non Final Office Action Issued in U.S. Appl. No. 15/936,076", dated Apr. 15, 2020, 23 Pages.

"Office Action Issued in European Patent Application No. 18708508.9", dated May 28, 2020, 6 Pages.

(56) References Cited

OTHER PUBLICATIONS

"Non Final Office Action Issued in U.S. Appl. No. 15/646,871", dated Jul. 1, 2020, 24 Pages.
"Final Office Action Issued in U.S. Appl. No. 15/657,822", dated Aug. 7, 2020, 22 Pages.
"Notice of Allowance Issued in U.S. Appl. No. 15/640,251", dated Jul. 31, 2020, 11 Pages.
"Final Office Action Issued in U.S. Appl. No. 16/005,470", dated Sep. 4, 2020, 15 Pages.

* cited by examiner

900

902 — DETECT PRESENCE OF A HUMAN USER AT A FIRST DETECTION POSITION WITHIN A FIELD-OF-DETECTION (FOD) OF THE FIRST INTELLIGENT ASSISTANT COMPUTING DEVICE

904 — LOCALIZE THE HUMAN USER TO A REAL-WORLD POSITION RELATIVE TO AN ENVIRONMENT OF THE FIRST INTELLIGENT ASSISTANT COMPUTING DEVICE CORRESPONDING TO THE FIRST DETECTION POSITION

906 — RECEIVE AN INDICATION THAT THE SECOND INTELLIGENT ASSISTANT COMPUTING DEVICE DETECTED THE HUMAN USER AT A SECOND DETECTION POSITION ALSO CORRESPONDING TO THE REAL-WORLD POSITION

908 — USING THE REAL-WORLD POSITION OF THE HUMAN USER AS A LANDMARK, ESTIMATE REAL-WORLD POSITIONS FOR EACH OF THE FIRST AND SECOND INTELLIGENT ASSISTANT COMPUTING DEVICES

FIG. 9

POSITION CALIBRATION FOR INTELLIGENT ASSISTANT COMPUTING DEVICE

CROSS REFERENCE TO RELATED APPLICATIONS

This application claims priority to U.S. Provisional Patent Application Ser. No. 62/459,020 filed Feb. 14, 2017, and to U.S. Provisional Patent Application Ser. No. 62/482,165 filed Apr. 5, 2017, the entirety of which are hereby incorporated herein by reference for all purposes.

BACKGROUND

Interacting with computing systems via natural interactions, such as one or more of voice recognition, text, gesture recognition, motion detection, gaze detection, intent recognition, brain activity assessment, text, the state of a home automated device, etc., enables natural user interface experiences.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A first intelligent assistant computing device configured to receive and respond to natural language inputs provided by human users syncs to a reference clock of a wireless computer network. The first intelligent assistant computing device receives a communication sent by a second intelligent assistant computing device indicating a signal emission time at which the second intelligent assistant computing device emitted a position calibration signal. The first intelligent assistant computing device records a signal detection time at which the position calibration signal was detected. Based on a difference between 1) the signal emission time and the signal detection time, and 2) a known propagation speed of the position calibration signal, a distance between the first and second intelligent assistant computing devices is calculated.

BRIEF DESCRIPTION OF THE DRAWINGS

FIG. 9 illustrates an example method for position calibration based on presence of a human user.

DETAILED DESCRIPTION

Figure 1:
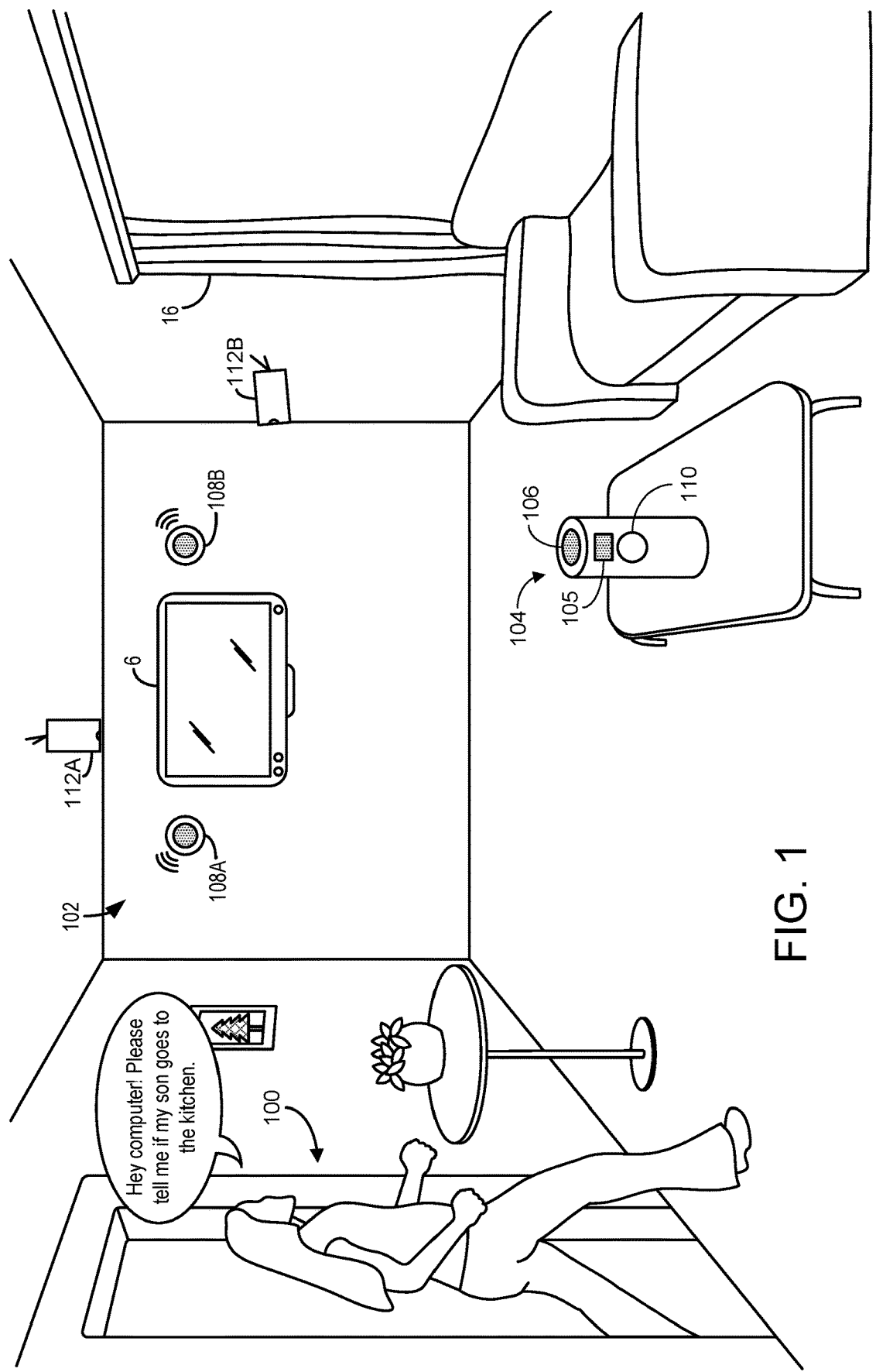
FIG. 1 shows an example environment with an intelligent assistant computing device.

As discussed above, many computing devices support natural language inputs, through which a human user can address and interact with a computing device in a manner that feels similar to addressing and interacting with another human. For example, a user may ask a virtual assistant provided by software running on an intelligent assistant computing device to provide a weather forecast, save a reminder, initiate a communication with another human, change the state of a device, etc. In a typical example, an intelligent assistant computing device may be implemented as an all-in-one computing device that a human user may place in their home, office, conference room, etc. Such devices may be equipped with microphones, cameras, speakers, video displays, and/or other suitable input/output devices useable for receiving, processing, and responding to natural language inputs.

However, such intelligent assistant computing devices are typically confined to single rooms, or individual subdivisions of rooms, outside of which their usefulness is limited. For example, a device's microphone can only record a human user's spoken natural language input when the user is close enough to be heard. This problem is often addressed by placing multiple intelligent assistant computing devices in the same room/building/environment. For instance, in a conference room setting, two or more intelligent assistant computing devices may be utilized to ensure that all individuals in the conference room are positioned close enough to an intelligent assistant computing device for their natural language inputs to be appropriately received and responded to.

However, this multi-device arrangement has its own associated set of challenges. For example, if a human user provides a natural language input that is detected by two intelligent assistant computing devices at the same time, both devices may attempt to respond, which can be both disconcerting for the human user, as well as a waste of computational resources. In another example, the human user may provide a natural language input to a first intelligent assistant computing device, then leave for a different room where a second, different intelligent assistant computing device is located. In this example, the first intelligent assistant computing device may attempt to respond to the natural language input, even though the human user is no longer present.

These problems could be at least partially mitigated if individual intelligent assistant computing devices had at least some information regarding their own positions relative to one another and/or their local environment. Accordingly, the present disclosure is directed to techniques for position calibration for an intelligent assistant computing device, by which the intelligent assistant computing device can calculate the distance between itself and another intelligent assistant computing device in its environment. With this information, multiple intelligent assistant computing devices can collectively respond to natural language inputs more efficiently. To reuse the examples from above, if two different intelligent assistant computing devices detect the same natural language input, the devices can determine which of them is closer to the human user who provided the input, enabling the better-positioned device to respond while the other device remains dormant. Similarly, as a user moves throughout multiple rooms in a house, responsibility for interacting with the user can be dynamically migrated from one intelligent assistant computing device to another, depending on which device the user is currently closest to. In other words, position calibration as described herein addresses numerous problems that arise in the field of computer technology, for example by allowing intelligent assistant computing devices to conserve both power and processing resources by only activating when appropriate.

FIG. 1 illustrates a human 100 entering a living room 102 with an example intelligent assistant computing device 104. As described in more detail below, in some examples computing device 104 may be configured to receive, process, and respond to natural language inputs. A "natural language input" may take any suitable form, such as spoken commands, hand gestures, text input, brain activity, etc. A human user may utilize the intelligent assistant computing device for myriad functions. For example, the user may provide natural language input to ask the intelligent assistant computing device to perform a variety of tasks, such as provide information, change the state of a device, send a message, complete a purchase, etc. Such natural language input may be detected, for example, by microphone 105, and/or other sensors of the intelligent assistant computing device. The intelligent assistant computing device may be configured to respond to natural language inputs audibly, for example via integrated speaker 106 or external speakers 108A and 108B. In another example, tasks may be performed programmatically without input from the user. For example, computing device 104 may utilize sensor data, such as audio and/or video data (e.g., received from integrated camera 110 or external cameras 112A and 112B) to detect when the user moves to another room and is looking at or "engaged" with another device. Using this data, computing device 104 may automatically alter the state of the device accordingly.

The user may ask the system for information about a wide range of topics, such as the weather, personal calendar events, movie show times, etc. In some examples, the intelligent assistant computing device also may be configured to control elements in the living room 102, such as external speakers 108A/108B, television 114, or motorized curtains 116.

The intelligent assistant computing device also may be utilized to receive and store messages and/or reminders to be delivered at an appropriate future time. Using data received from sensors, the intelligent assistant computing device may track and/or communicate with one or more users or other entities.

In some examples, the computing device 104 may be operatively connected with one or more other computing devices using a wired connection, or may employ a wireless connection via Wi-Fi, Bluetooth, or any other suitable wireless communication protocol. For example, the computing device 104 may be communicatively coupled to one or more other computing devices via a computer network. The network may take the form of a local area network (LAN), wide area network (WAN), wired network, wireless network, personal area network, or a combination thereof, and may include the Internet. As will be discussed in more detail, in some settings it may be beneficial for multiple intelligent assistant computing devices in an environment to communicate over a wireless computer network, such that each device learns its position relative to the other computing devices.

It will be appreciated that the computing device 104 of FIG. 1 is merely one example implementation of the intelligent assistant computing device of the present disclosure, and any suitable computer hardware may be used, having any suitable form factor. Additional details regarding components and computing aspects of the computing device 104 are described in more detail below with reference to FIG. 13.

Figure 2:
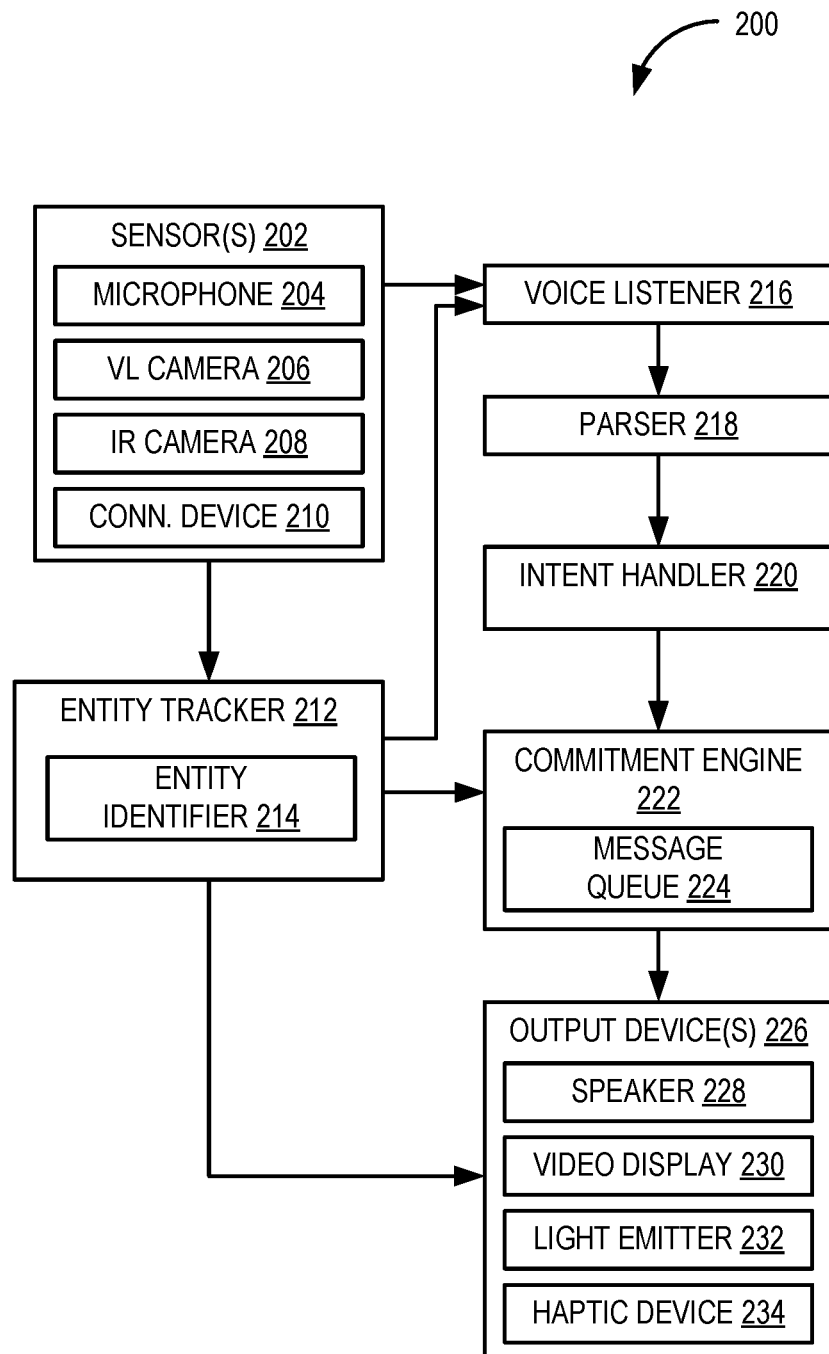
FIG. 2 schematically shows an example architecture for implementing an intelligent assistant computing device.

FIG. 2 shows an example architecture for implementing a computing system 200 capable of recognizing and responding to natural language inputs according to examples of the present disclosure. Intelligent assistant computing device 104 of FIG. 1 is one example implementation of computing system 200. However, it will be understood that the various components and functional elements of system 200 may be distributed between any suitable number of computing devices. For example, components shown in FIG. 2 may be collectively provided in a single computing device, a pair of distinct devices in the same environment communicating over a local network, one or more devices communicating over the Internet with a plurality of cloud servers configured for remote processing, etc.

In this example the computing system 200 includes at least one sensor 202, an entity tracker 212, a voice listener 216, a parser 218, an intent handler 220, a commitment engine 222, and at least one output device 226. In some examples the sensors 202 may include one or more microphones 204, visible light cameras 206, infrared (IR) cameras 208, and connectivity devices 210, such as Wi-Fi or Bluetooth modules. In some examples sensor(s) 202 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 212 is configured to detect entities and their activities, including people, animals, or other living things, as well as non-living objects (e.g., intelligent assistant computing devices). Entity tracker 212 includes an entity identifier 214 that is configured to recognize individual users and/or non-living objects. Voice listener 216 receives audio data and utilizes speech recognition functionality to translate spoken utterances into text. Voice listener 216 also may assign confidence value(s) to the translated text, and may perform speaker recognition to determine an identity of the person speaking, as well as assign probabilities to the accuracy of such identifications. Parser 218 analyzes text and confidence values received from voice listener 216 to derive user intentions and generate corresponding machine-executable language.

Intent handler 220 receives machine-executable language representing user intentions from the parser 218, and resolves missing and ambiguous information to generate commitments. Commitment engine 222 stores commitments from the intent handler 220. At a contextually appropriate time, the commitment engine may deliver one or more messages and/or execute one or more actions that are associated with one or more commitments. Commitment engine 222 may store messages in a message queue 224 or cause one or more output devices 226 to generate output. The output devices 226 may comprise one or more of speaker(s) 228, video display(s) 230, light emitter(s) 232, haptic device(s) 234, and/or other suitable output devices. In other examples, output devices 226 may comprise one or more other devices or systems, such as home lighting, thermostats, media programs, door locks, etc., that may be controlled via actions executed by the commitment engine 222.

In different examples the voice listener 216, parser 218, intent handler 220, commitment engine 222, and/or entity tracker 212 may be embodied in software that is stored in memory and executed by one or more processors of a computing device. In some implementations, specially programmed logic processors may be utilized to increase the computational efficiency and/or effectiveness of the intelligent assistant computing device. Additional details regarding the components and computing aspects of computing devices that may store and execute these modules are described in more detail below with reference to FIG. 13.

With reference again to FIG. 2, in some examples the voice listener 216 and/or commitment engine 222 may receive context information including associated confidence values from entity tracker 212. As described in more detail below, entity tracker 212 may determine an identity, position, and/or current status of one or more entities within range of one or more sensors, and may output such information to one or more other modules, such as voice listener 216, commitment engine 222, etc. In some examples, entity tracker 212 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

Furthermore, in some examples, entity tracker 212 may be configured to interface with and/or coordinate the activity of one or more of the output devices 226. As discussed above, it is often desirable for individual intelligent assistant computing devices in an environment to have at least some information regarding their positions relative to each other and/or relative to the environment. In this manner, the intelligent assistant computing devices can respond more effectively to human user input collectively, for instance by automatically handing off interaction responsibilities as the human user moves throughout the environment. To this end, the entity tracker may utilize one or both of the sensors 202 and output devices 226 to emit and/or receive position calibration signals useable to calculate the distance between intelligent assistant computing devices in the same environment. The entity tracker may save a map or other information useable to track the relative positions of the various intelligent assistant computing devices. In some implementations, such a map or other information may be saved locally on one or more intelligent assistant computing devices. In some implementations, such a map or other information may be saved remotely. When saved remotely, one or more intelligent assistant computing devices may access the remotely saved map and/or other information.

Figure 3:
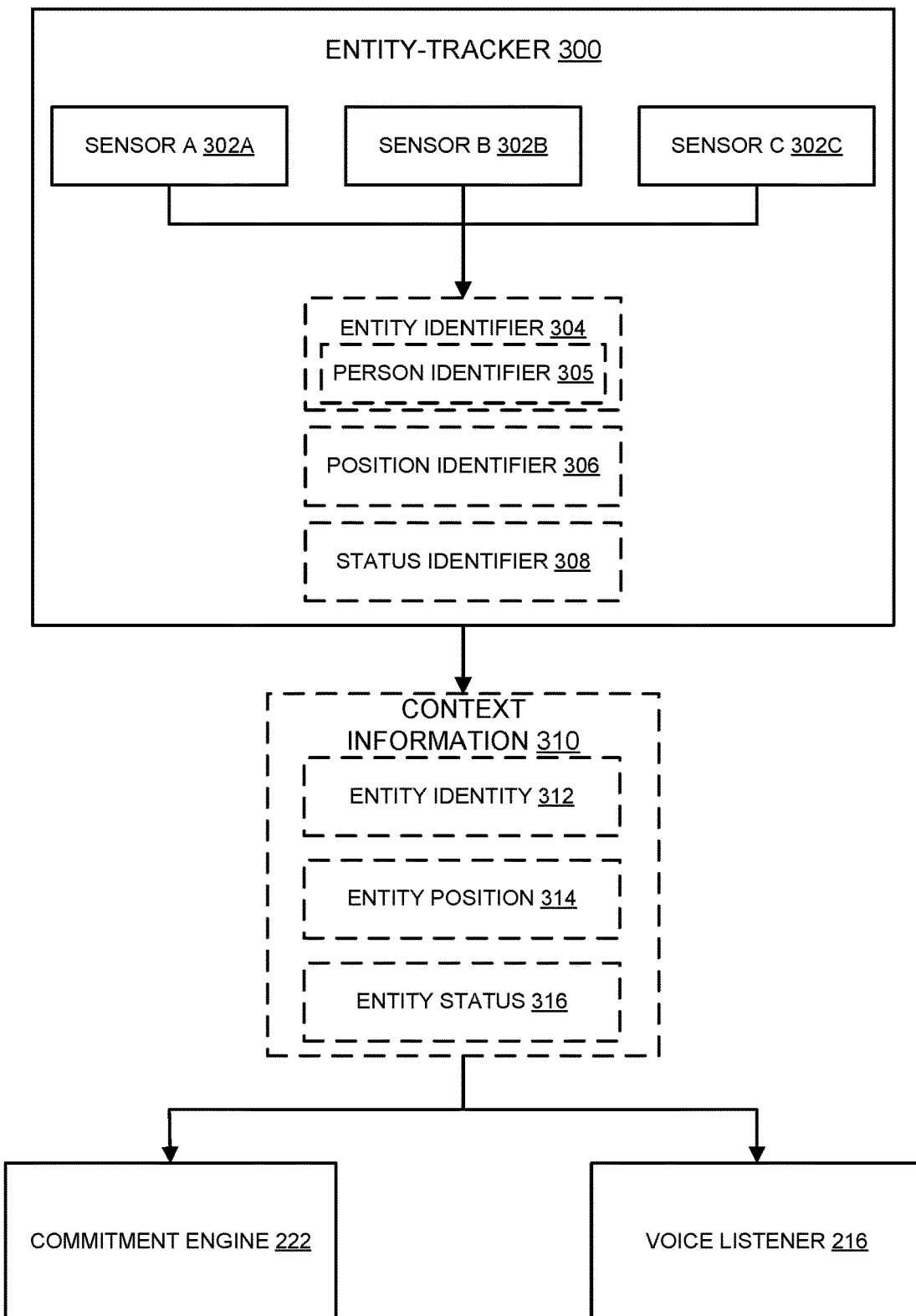
FIG. 3 schematically shows an example entity tracker of an intelligent assistant computing device.

FIG. 3 schematically illustrates an example entity tracker 300 that may, in some examples, comprise a component of an intelligent assistant computing device as described herein. Entity tracker 300 may be used to determine an identity, position, and/or current status of one or more entities within range of one or more sensors. Entity tracker 300 may output such information to one or more other modules of computing system 200, such as the commitment engine 222, voice listener 216, etc.

The word "entity" as used in the context of the entity tracker 300 may refer to people, animals, or other living things, as well as non-living objects. For example, the entity tracker may be configured to identify furniture, appliances, autonomous robots, other intelligent assistant computing devices, structures, landscape features, vehicles, and/or any other physical object, and determine the position/location and current status of such physical objects.

Entity tracker 300 receives sensor data from one or more sensors 302, such as sensor A 302A, sensor B 302B, and sensor C 302C, though it will be understood that an entity tracker may be used with any number and variety of suitable sensors. As examples, sensors usable with an entity tracker may include cameras (e.g., visible light cameras, UV cameras, IR cameras, depth cameras, thermal cameras), microphones, directional microphone arrays (i.e., a beamforming microphone array), pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalograms), automotive sensors (e.g., speedometers, odometers, tachometers, fuel sensors), and/or any other sensors or devices that collect and/or store information pertaining to the identity, position, and/or current status of one or more people or other entities. In some examples, the entity tracker 300 may occupy a common device housing with one or more of the plurality of sensors 302, and/or the entity tracker and its associated sensors may be distributed across multiple devices configured to communicate via one or more network communications interfaces (e.g., Wi-Fi adapters, Bluetooth interfaces).

As shown in the example of FIG. 3, entity tracker 300 may include an entity identifier 304, a person identifier 305, a position (location) identifier 306, and a status identifier 308. In some examples, the person identifier 305 may be a specialized component of the entity identifier 300 that is particularly optimized for recognizing people, as opposed to other creatures and non-living things. In other cases, the person identifier 305 may operate separately from the entity identifier 304, or the entity tracker 100 may not include a dedicated person identifier.

Depending on the specific implementation, any or all of the functions associated with the entity identifier, person identifier, position identifier, and status identifier may be performed by the individual sensors 302A-302C. Though the present description generally describes the entity tracker 300 as receiving data from sensors, this does not require that the entity identifier 304, as well as other modules of the entity tracker, must be implemented on a single computing device that is separate and distinct from the plurality of sensors associated with the entity tracker. Rather, functions of the entity tracker 300 may be distributed amongst the plurality of sensors, or other suitable devices. For example, rather than sending raw sensor data to the entity tracker, individual sensors may be configured to attempt to identify entities that they detect, and report this identification to the entity tracker 300, and/or other modules of computing system 200. Furthermore, to simplify descriptions below, the term "sensor" is sometimes used to describe not only the physical measurement device (e.g., microphone or camera), but also the various logic processors configured and/or programmed to interpret signals/data from the physical measurement devices. For example, a "microphone" may be used to refer to the device that translates acoustic energy to an electrical signal, the analog-to-digital converter that converts the electrical signal to digital data, the on-board application-specific-integrated-circuit that pre-processes the digital data, and the downstream modules described herein (e.g., entity tracker 300, entity identifier 304, voice listener 216, or parser 218). As such, reference to a generic "sensor" or a particular sensor (e.g., "microphone" or "camera") should not be construed to mean only the physical measurement device, but also the cooperating modules/engines, which can be distributed across one or more computers.

Each of the entity identifier 304, person identifier 305, position identifier 306, and status identifier 308 is configured to interpret and evaluate sensor data received from the plurality of sensors 302, and to output context information 310 based on the sensor data. Context information 310 may include the entity tracker's guesses/predictions as to an identity, position, and/or status of one or more detected entities based on received sensor data. As will be described in more detail below, each of the entity identifier 304, person identifier 305, position identifier 306, and status identifier 308 may output their predictions/identifications along with a confidence value.

The entity identifier 304, person identifier 305, position identifier 306, status identifier 308, and other processing modules described herein may utilize one or more machine-learning technologies. Non-limiting examples of such machine-learning technologies can include Feedforward Networks, Recurrent Neural Networks (RNN), Long Short-term Memory (LSTM), Convolutional Neural Networks, Support-vector Machines (SVM), Generative-Adversarial Networks (GAN), Variational Autoencoders, Q-Learning, and Decision Trees. The various identifiers, engines, and other processing blocks described herein may be trained via supervised and/or unsupervised learning utilizing these, or any other appropriate, machine learning technologies to make the described assessments, decisions, identifications, etc. It should be understood, however, that this description is not intended to put forth new technologies for making such assessments, decisions, identifications, etc. Instead, this description is intended to manage computational resources, and as such, is meant to be compatible with any type of processing module.

The entity identifier 304 may output an entity identity 312 of a detected entity, and such entity identity may have any suitable degree of specificity. In other words, based on received sensor data, the entity tracker 300 may predict the identity of a given entity, and output such information as entity identity 312. For example, the entity identifier 304 may report that a particular entity is a piece of furniture, a computing device, a dog, a human male, etc. Additionally, or alternatively, the entity identifier 304 may report that a particular entity is an intelligent assistant computing device with a particular model number and/or user-assigned device name; a pet dog with a specific name and breed; an owner or known user of an intelligent assistant computing device, the owner/known user having a particular name and profile; etc. In some examples, the degree of specificity with which the entity identifier 304 identifies/classifies detected entities may depend on one or more of user preferences and sensor limitations. In some cases, the entity identity output by the entity identifier may simply be a generic identifier that provides no information regarding the nature of the tracked entity, but rather is used to distinguish one entity from another.

The position identifier 306 may be configured to output an entity position (i.e., location) 314 of a detected entity. In other words, the position identifier 306 may predict the current position of a given entity based on collected sensor data, and output such information as entity position 314. As with the entity identity 312, the entity position 314 may have any suitable level of detail, and this level of detail may vary with user preferences and/or sensor limitations. For example, the position identifier 306 may report that a detected entity has a two-dimensional position defined on a plane such as a floor or wall. Additionally, or alternatively, the reported entity position 314 may comprise a three-dimensional position of a detected entity within a real world, three-dimensional environment. In some examples an entity position 314 may comprise a GPS position, a location within an environment-relative coordinate system, etc. In other examples, the entity position may be defined relative to the position of the intelligent assistant computing device. As will be described in more detail below, after performing position calibration, an entity tracker may in some cases calculate a distance between two different intelligent assistant computing devices.

The reported entity position 314 for a detected entity may correspond to the entity's geometric center, a particular part of the entity that is classified as being important (e.g., the head of a human), a series of boundaries defining the borders of the entity in three-dimensional space, etc. The position identifier 306 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 314 of a detected entity may be reported even if the entity tracker 300 is unable to identify the entity, and/or determine the current status of the entity.

Status identifier 308 may be configured to output an entity status 316 of a detected entity. In other words, the entity tracker 300 may be configured to predict the current status of a given entity based on received sensor data, and output such information as entity status 316. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

Upon determining one or more of the entity identity 312, entity position 314, and entity status 316, such information may be sent as context information 310 to any of a variety of external modules or devices, where it may be used in a variety of ways. For example, context information 310 may be used by commitment engine 222 to manage commitments and associated messages and notifications. In some examples, context information 310 may be used by commitment engine 222 to determine whether a particular message, notification, or commitment should be executed and/or presented to a user. Similarly, context information 310 may be utilized by voice listener 216 when interpreting human speech or activating functions in response to a keyword trigger.

Each of entity identity 312, entity position 314, and entity status 316 may take any suitable form. For example, each of the entity identity 312, position 314, and status 316 may take the form of a discrete data packet including a series of values and/or labels describing the information gathered by the entity tracker. Each of the entity identity 312, position 314, and status 316 may additionally include a confidence value defining a statistical likelihood that the information is accurate. For example, if the entity identifier 304 receives sensor data that strongly indicates that a particular entity is a human male named "John Smith," then entity identity 312 may include this information along with a corresponding relatively high confidence value, such as 90% confidence. If the sensor data is more ambiguous, then the confidence value included in entity identity 312 correspondingly may be relatively lower, such as 62%. In some examples, separate predictions may be assigned separate confidence values. For example, the entity identity 312 may indicate with 95% confidence that a particular entity is a human male, and indicate with a 70% confidence that the entity is John Smith. Such confidence values (or probabilities) may be utilized by a cost function in generating cost calculations for providing messages or other notifications to a user and/or performing action(s).

As noted above, in some examples the entity tracker 300 may be implemented in a single computing device. In other examples, one or more functions of the entity tracker 300 may be distributed across multiple computing devices working cooperatively. For example, one or more of the entity identifier 304, person identifier 305, position identifier 306, and status identifier 308 may be implemented on different computing devices, while still collectively comprising an entity tracker configured to perform the functions described herein. As indicated above, any or all of the functions of the entity tracker may be performed by individual sensors 302. Further, in some examples entity tracker 300 may omit one or more of the entity identifier 304, person identifier 305, position identifier 306, and status identifier 308, and/or include one or more additional components not described herein, while still providing context information 310. Additional details regarding components and computing aspects that may be used to implement entity tracker 300 are described in more detail below with respect to FIG. 13.

Returning briefly to FIG. 1, intelligent assistant computing device 104 is illustrated as a unified all-in-one device. In other words, computing device 104 may include any/all of the components of computing system 200 described above with respect to FIG. 2, including one or more processors, sensors, output devices, etc. However, as discussed above, a single intelligent assistant computing device may not be sufficient to adequately provide intelligent assistance to all human users in an environment, such as a conference room or residence. For example, should human user 100 leave living room 102, then intelligent assistant computing device 104 may no longer be capable of adequately receiving and responding to natural language inputs provided by human user 102.

This problem may be mitigated by distributing additional intelligent assistant computing devices throughout the environment, thereby increasing the available space in which intelligent assistance is available. Such a distributed arrangement may be referred to as a "mesh" of devices. In other words, should human user 100 leave living room 102, she may direct additional natural language inputs to a different intelligent assistant computing device located in a different room. However, as discussed above, this scenario has its own associated drawbacks, for example when two different intelligent assistant computing devices receive the same natural language input and attempt to respond, or when intelligent assistant computing device 104 remains active even when the human user has left living room 102.

This can be at least partially alleviated when individual intelligent assistant computing devices in the environment each have at least some information regarding their positions relative to each other and/or the overall environment. Such information may be derived in a variety of ways, as will be discussed in more detail below. In some examples, one or both of the intelligent assistant computing devices may emit a position calibration signal detectable by the other intelligent assistant computing device(s). Upon receiving the position calibration signal, an intelligent assistant computing device can analyze the signal to calculate the distance between the intelligent assistant computing device that received the position calibration signal and the intelligent assistant computing device that emitted the position calibration signal. This may involve, for example, multiplying the time it took the position calibration signal to travel between the two devices with a known propagation speed of the position calibration signal. As used herein, processes through which an intelligent assistant computing device receives information regarding the position of another intelligent assistant computing device are referred to as "position calibration."

Figure 4:
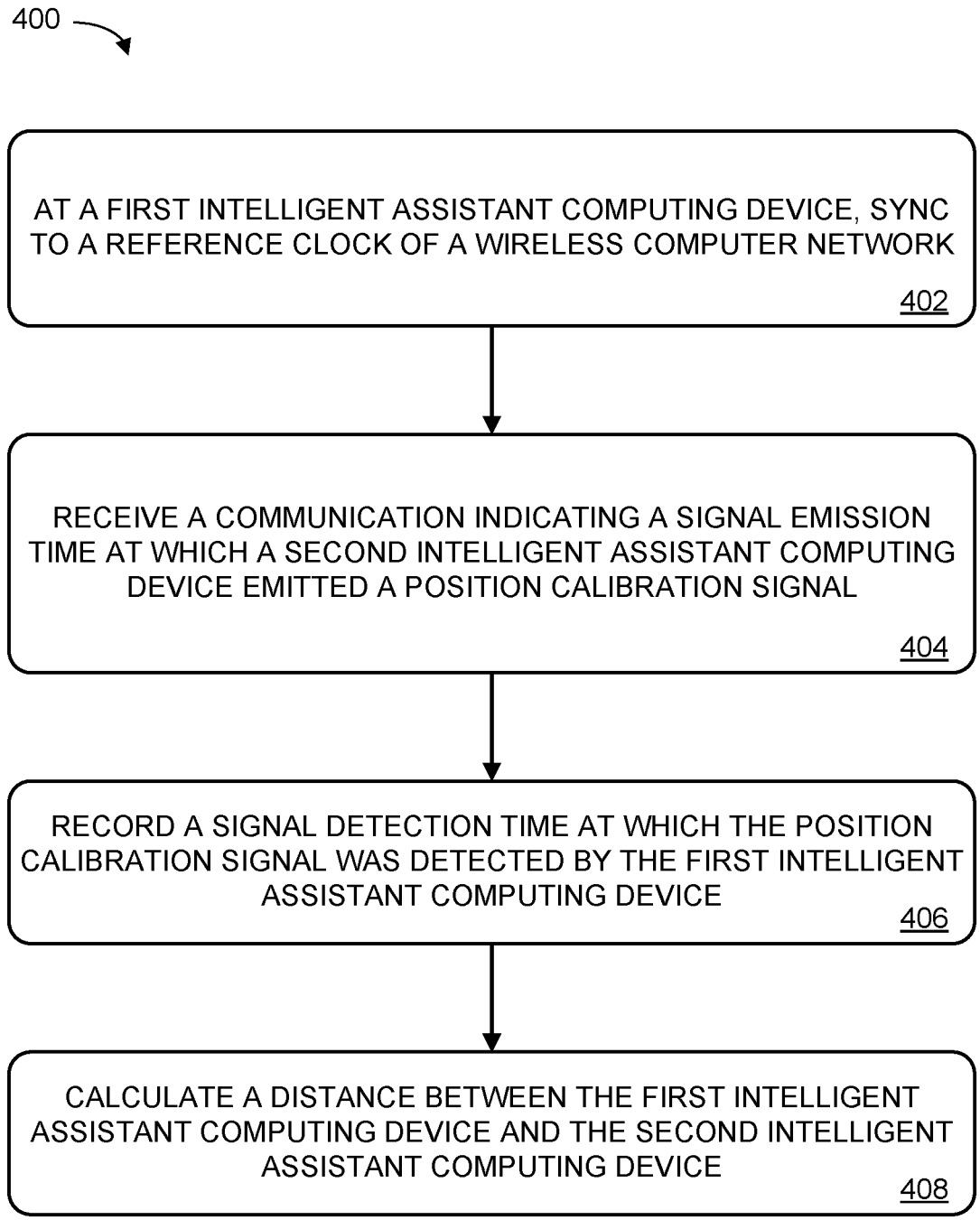
FIG. 4 illustrates an example method for position calibration for an intelligent assistant computing device.

FIG. 4 illustrates an example method 400 of position calibration for intelligent assistant computing devices. While method 400 may be implemented on relatively stationary "all-in-one" intelligent assistant computing devices, such as device 104 shown in FIG. 1, it will be understood that method 400 may be implemented on any computer hardware suitable for receiving, processing, and responding to natural language inputs. For example, method 400 may be implemented on a user's smartphone or other mobile device, desktop computer, media center, virtual/augmented reality computing device, etc. In some examples, all or part of method 400 and/or other methods described herein may be at least partially implemented with the assistance of one or more computing platforms that communicate with the intelligent assistant computing device(s) (e.g., a cloud computing service). In particular, any number of the processing/calculating/analysis steps described herein may be distributed between any number of computing systems, including remote computing systems. In some examples, method 400 may be implemented on computing system 1300 described below with respect to FIG. 13.

Depending on the nature of the position calibration signal, calculating the distance between the two intelligent assistant computing devices will sometimes be more accurate when one intelligent assistant computing device has accurate information regarding when the position calibration signal was emitted by the other intelligent assistant computing device. With respect to FIG. 4, the device that detects the position calibration signal will be referred to as the "first intelligent assistant computing device," and the device that emits the position calibration signal will be referred to as the "second intelligent assistant computing device."

At 402, method 400 includes, at the first intelligent assistant computing device, syncing to a reference clock of a wireless computer network. Notably, the reference clock is supported by the second intelligent assistant computing device, which is communicatively coupled to the first intelligent assistant computing device via the wireless computer network.

Different intelligent assistant computing devices may each maintain their own internal clock., which can complicate the coordination between the devices involved in position calibration. Accordingly, during synchronization, the internal clock of either or both devices may be adjusted to match the reference clock. Synchronizing to the reference clock can therefore involve one device adjusting its internal clock to match the internal clock of the other device (i.e., the second intelligent assistant computing device provides the reference clock), or both devices adjusting their internal clocks to match a reference clock provided by a $3^{rd}$ party. In this manner, the two intelligent assistant computing devices can achieve a shared sense of time.

In other examples, synchronization may occur without adjusting or altering a device's internal clock. Rather, for example, an intelligent assistant computing device may merely record an offset between its own internal clock and the reference clock, such that it can report events to other devices relative to the reference clock rather than its own internal clock.

It will be understood that the reference clock can take any suitable form. As examples, the reference clock may be the internal clock maintained by an intelligent assistant computing device, the reference clock as modified by a sync offset, a clock maintained by local network infrastructure (e.g., a wireless router or modem), a clock maintained by a remote timekeeping service (e.g., an Internet Service Provider or intelligent assistant computing device manufacturer), etc.

Figure 5A:
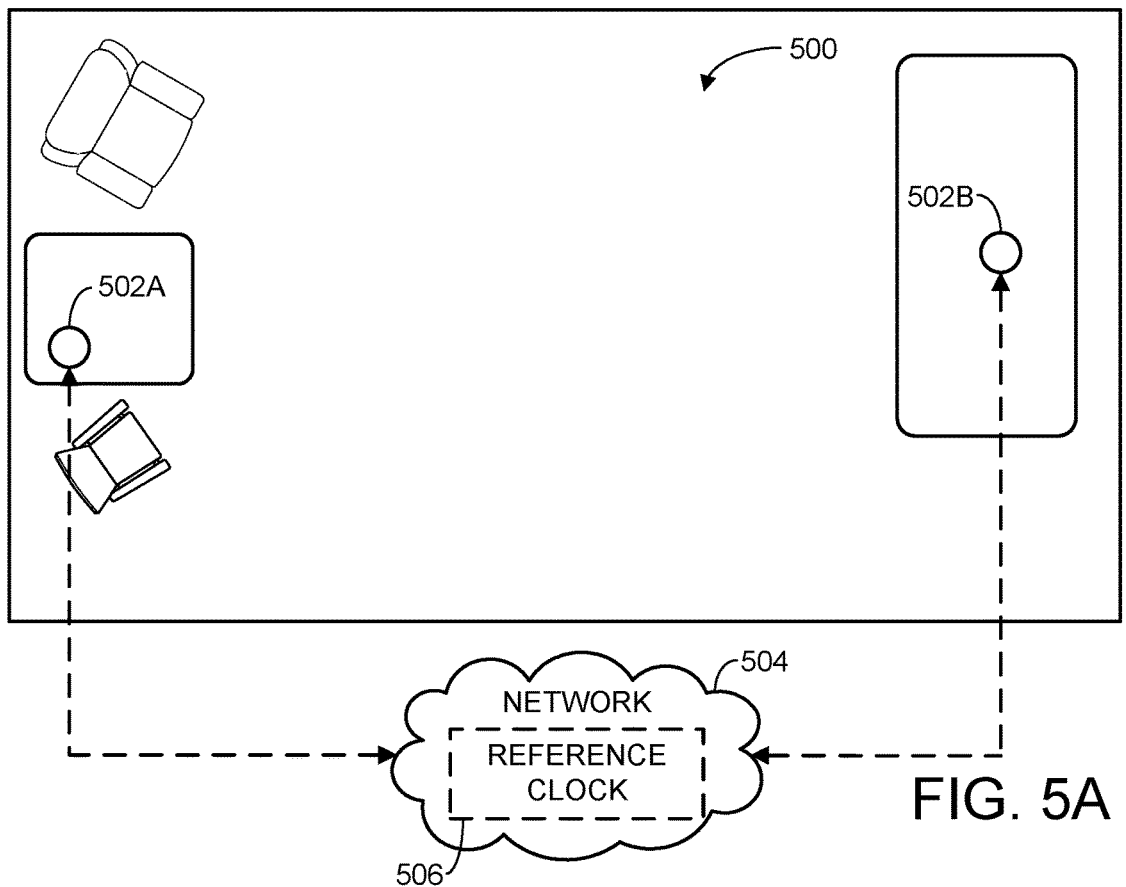
FIGS. 5A-5D schematically illustrate receipt of a position calibration signal by an intelligent assistant computing device.

Method 400 is schematically illustrated with respect to FIGS. 5A-5D. Specifically, FIG. 5A shows an example environment 500 including a first intelligent assistant computing device 502A and a second intelligent assistant computing device 502B. Computing devices 502A and 502B are wirelessly coupled via wireless computer network 504, which maintains a reference clock 506. In this example, the reference clock is maintained by a network device in environment 500, such as a Wi-Fi router. Each of the intelligent assistant computing devices synchronize to the reference clock, thereby achieving a shared sense of time.

As discussed above, during position calibration, one intelligent assistant computing device may emit a position calibration signal that is received and analyzed by the other intelligent assistant computing device to calculate the distance between the two devices, and/or derive information regarding the devices' relative positions.

Turning back to FIG. 4, at 404, method 400 includes receiving a communication sent by the second intelligent assistant computing device over the wireless computer network, the communication indicating a signal emission time at which the second intelligent assistant computing device emitted the position calibration signal. The communication may take any suitable form, though in most cases will encode one or more computer data packets (e.g., network packets) specifying the signal emission time and any associated metadata.

In some cases, the signal emission time may be defined relative to the reference clock. For example, if the reference clock is currently at 0:00:00, then the signal emission time may indicate that the position calibration signal was emitted at 0:00:00, even if, for example, the internal clock of the second intelligent assistant computing device currently reports a different time. In a different scenario, the signal emission time may be reported according to the internal clock of the second intelligent assistant, along with accompanying data describing the offset between the reported time and the reference clock. The signal emission time may be expressed in other suitable ways, for instance by reference to a numbered time frame recorded by the second intelligent assistant computing device. In an example scenario, both intelligent assistant computing devices may establish the moment of synchronization with the reference clock as "time frame 0," and begin tracking time frames synchronously thereafter. Each time frame may last any suitable length of time, such as, for example, one millisecond.

In some examples, the communication may be sent before the position calibration signal is emitted, in which case the signal emission time will be a future time. In other examples, the communication may be sent simultaneously with the emission of the position calibration signal, or after the emission of the position calibration signal. In general, the signal emission time may be reported in any manner or format useable by the first intelligent assistant computing device to accurately infer when the position calibration signal was or will be emitted.

Figure 5B:
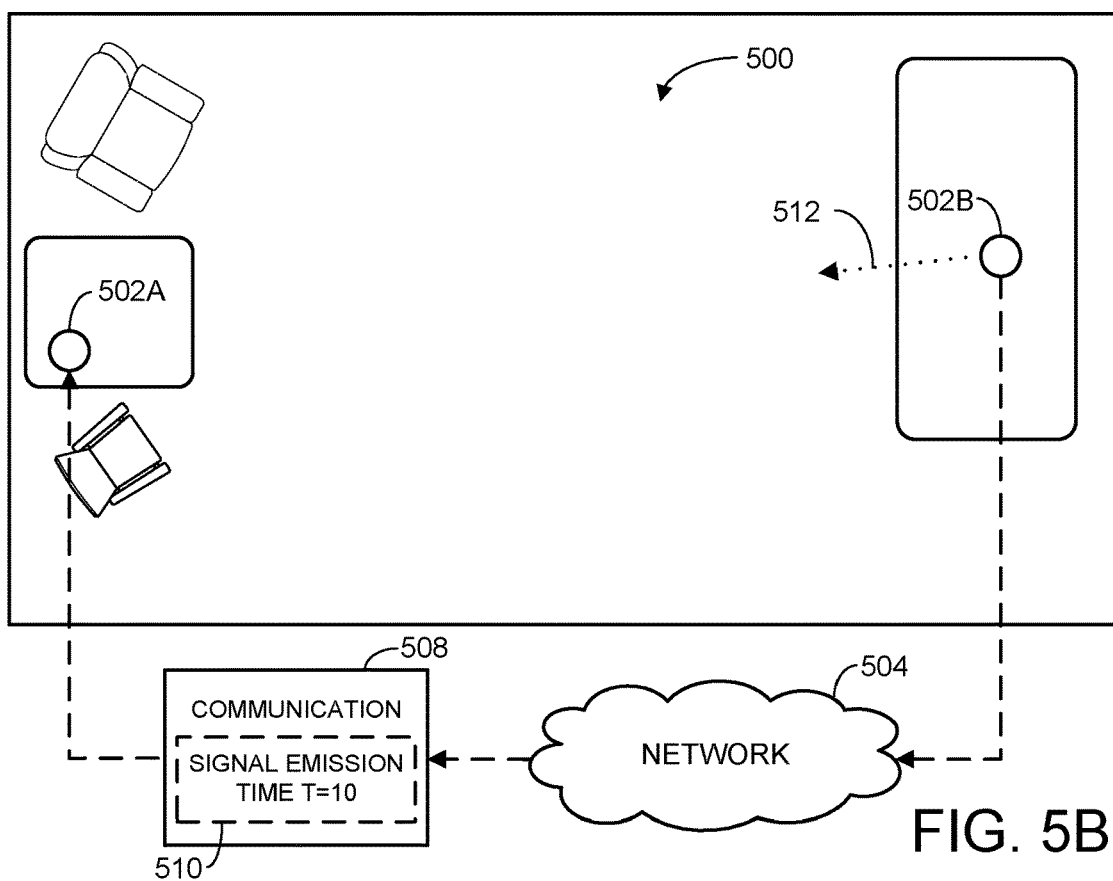

FIG. 5B shows environment 500 along with first and second intelligent assistant computing devices 502A and 502B. In FIG. 5B, second intelligent assistant computing device 502B has sent a communication 508 to first intelligent assistant computing device 502A via wireless computer network 504. Communication 508 includes a signal emission time 510, which in this example indicates that the position calibration signal was emitted at T=10—e.g., time frame 10.

Second intelligent assistant computing device 502B has also emitted a position calibration signal 512. The position calibration signal may take a variety of suitable forms, and be transmitted over any suitable medium. In the example of FIGS. 5A-5D, the position calibration signal is an emission of sound produced by one or more speakers of second intelligent assistant computing device 502B. The emission of sound may include any suitable number of different frequencies. For example, the emission of sound may have a single frequency, having any suitable pitch. In other examples, the emission of sound may include a plurality of frequencies. This may be advantageous in some scenarios, as different frequencies of sound often have varying degrees of directionality depending on pitch (i.e., lower pitches are often less directional than higher pitches). Furthermore, one or more of the plurality of frequencies may be ultrasonic frequencies. Ultrasonic frequencies have the advantage of being inaudible, and therefore not distracting, to nearby humans.

Returning briefly to FIG. 4, at 406, method 400 includes recording a signal detection time at which the position calibration signal was detected by the first intelligent assistant computing device. The position calibration signal may be detected in any suitable way, depending on the nature of the position calibration signal. For instance, when the position calibration signal is an emission of sound (as is the case in FIGS. 5A-5D), the position calibration signal may be detected by a microphone of the first intelligent assistant computing device (e.g., microphone 105 of intelligent assistant computing device 104). Any suitable microphone may be used, though the microphone may optionally be implemented as a beamforming microphone array. This may allow the first intelligent assistant device to calculate the direction from which the position calibration signal was emitted, as will be discussed below.

Figure 5C:
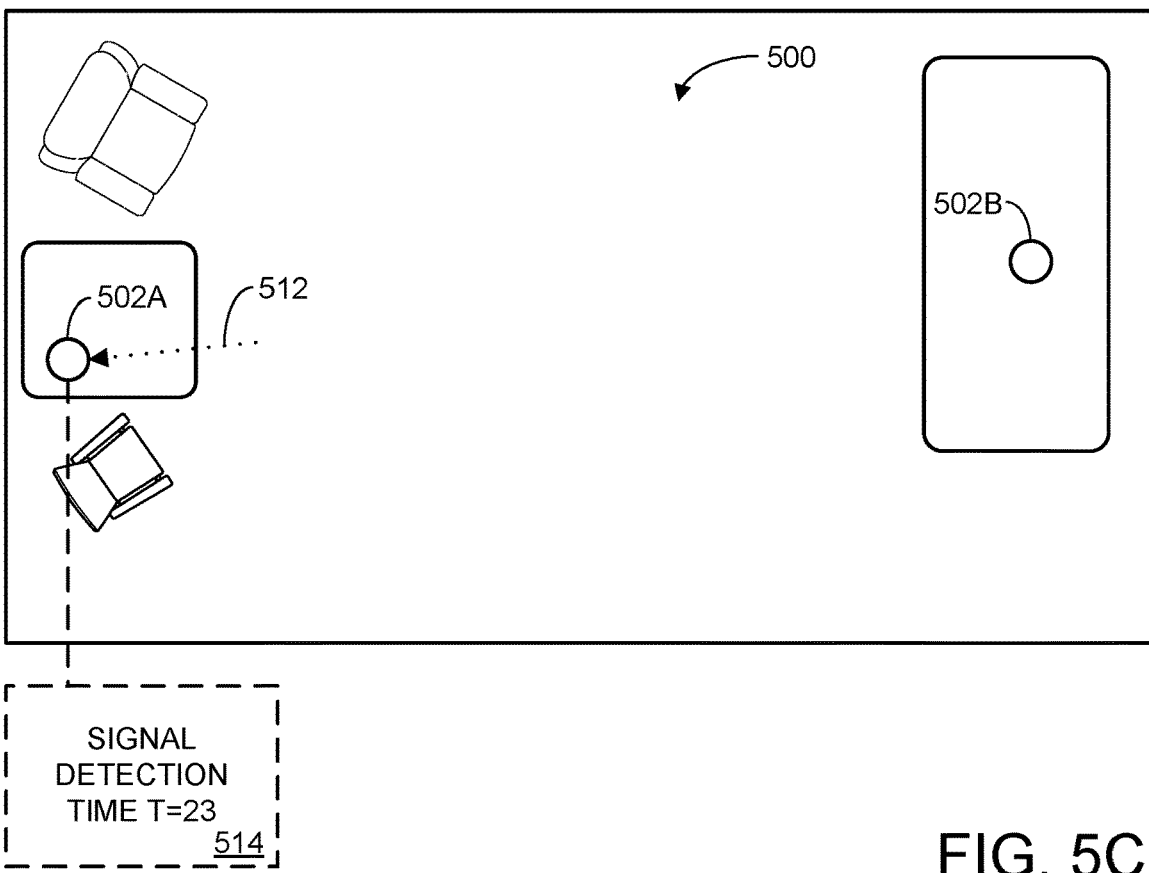
Figure 5D:
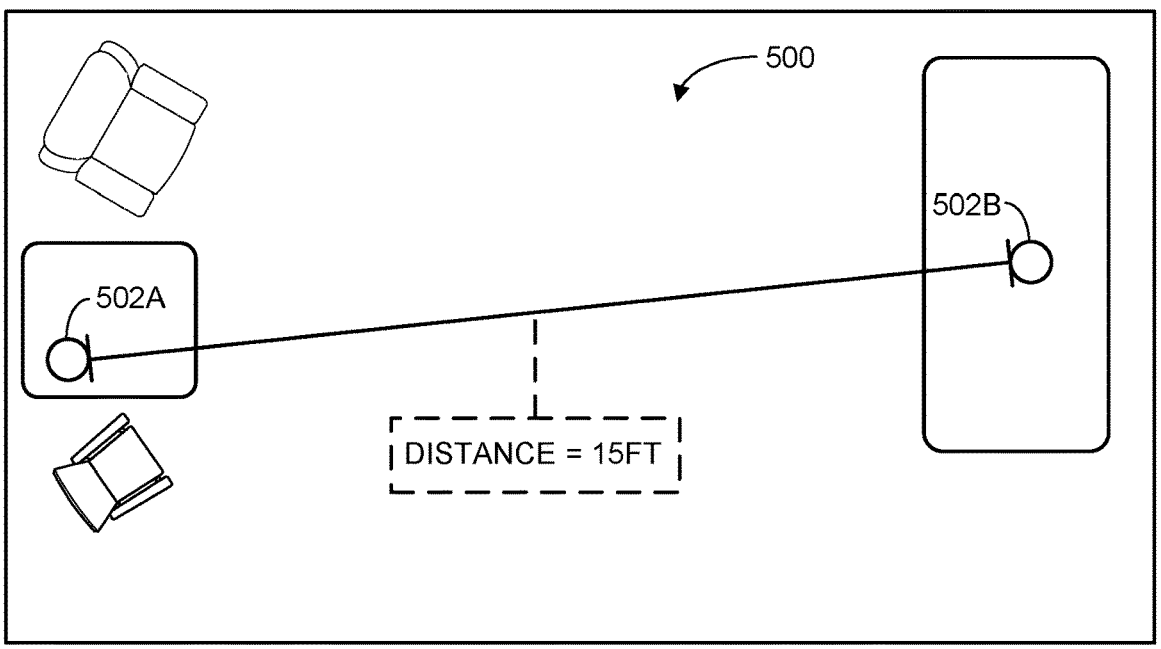

In FIG. 5C, position calibration signal 512 has traveled across environment 500 and is detected by first intelligent assistant computing device 502A. Upon detection of the position calibration signal, the first intelligent assistant computing device records a signal detection time 514. In general, the signal detection time may be defined in any suitable way, using any suitable time scale or data format. As with the signal emission time, the signal detection time may in some cases be defined relative to the reference clock. In this case, the signal detection time is T=23, or thirteen time frames after the position calibration signal was emitted. As indicated above, in some cases each time frame may have a length of one millisecond.

In addition to or as an alternative to recording the signal detection time, the first intelligent assistant computing device may record a direction from which the position calibration signal was received (e.g., when the position calibration signal is detected via a beamforming microphone array), a volume/amplitude of the detected position calibration signal, and/or other suitable parameters. The direction from which the position calibration signal was detected can in some cases correspond to the direction at which the second intelligent assistant computing device is positioned relative to the first intelligent assistant computing device. Similarly, the volume/amplitude of the detected position calibration signal can aid in calculating the distance between the first and second intelligent assistant computing devices when an original emission volume/amplitude of the position calibration signal is also known.

Returning briefly to FIG. 4, at 408, method 400 includes, based at least on a difference between the signal emission time and the signal detection time and a known propagation speed of the position calibration signal, calculating a distance between the first and second intelligent assistant computing devices. At a basic level, by subtracting the signal emission time from the signal detection time, the time-of-flight for the position calibration signal may be calculated. By multiplying the time-of-flight by the known propagation speed, the distance between the intelligent assistant computing devices may be calculated. In the example of FIG. 5, the time-of-flight of the position calibration signal (0.013 seconds) may be multiplied by the known speed of sound (approx. 1,125 feet/second) to give an estimated distance between the two intelligent assistant devices of approximately 15 feet. It will be understood that the above calculation is a simplified example, and in some cases more complicated calculations may be performed, for example to account for network latency, signal interference, reflections of the position calibration signal, etc. In one example, the amplitude of a detected emission of sound (e.g., volume or "loudness") may be compared to a known emission amplitude of the emission of sound, and this may be used to augment the distance calculation described above, for example based on a known or estimated amplitude falloff/decay of the position calibration signal.

Furthermore, the term "calculation" is used herein broadly, and may refer to one or more operations not locally performed by the first intelligent assistant computing device. Calculating may in some cases include sending data (e.g., the signal detection and emission times, other data relating to the position calibration signal, environment, or intelligent assistant computing devices) to one or more other local or remote computing devices for processing and analysis. In one example, such data may be sent to a cloud service, which may perform some or all of the calculations described herein, and transmit the results of such calculations to any or all intelligent assistant computing devices in the environment.

Figure 6:
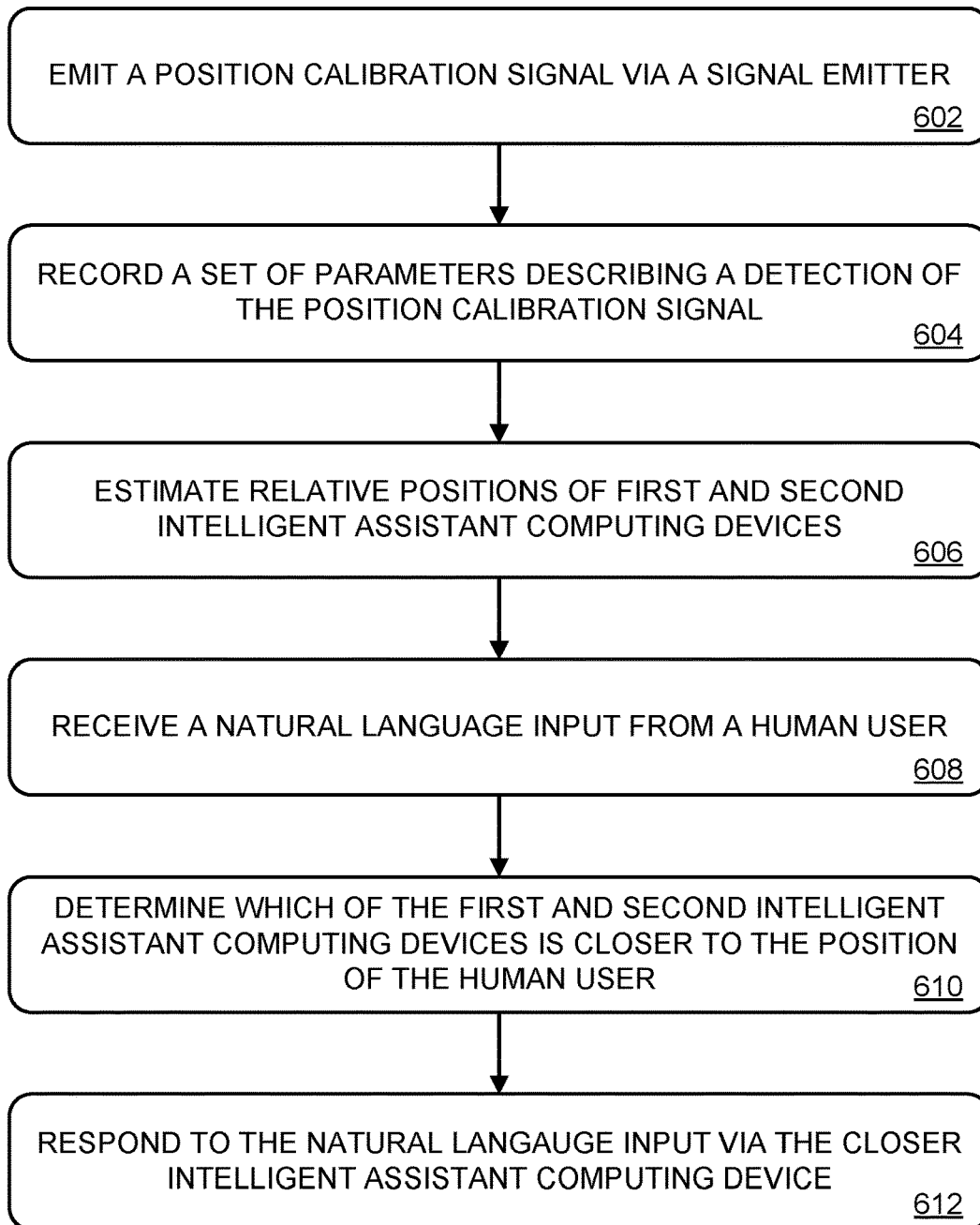
FIG. 6 illustrates another example method for position calibration for an intelligent assistant computing device.

As indicated above, an intelligent assistant computing device may emit other types of position calibration signals besides sound. FIG. 6 illustrates another example method 600 for position calibration for intelligent assistant computing devices, in which the position calibration signal is an emission of light. As with method 400, method 600 will may be implemented on relatively stationary "all-in-one" intelligent assistant computing devices, such as device 104 shown in FIG. 1. However, it will be understood that method 600 may be implemented on any computer hardware suitable for receiving, processing, and responding to natural language inputs. In some examples, method 600 may be implemented on computing system 1300 described below with respect to FIG. 13.

At 602, method 600 includes, at a first intelligent assistant computing device, emitting a position calibration signal via a signal emitter. With respect to FIG. 6, the device that emits the position calibration signal will be referred to as the "first intelligent assistant computing device," and the device that detects the position calibration signal will be referred to as the "second intelligent assistant computing device."

In the example of FIG. 6, the position calibration signal is an emission of light. Accordingly, the signal emitter may be a suitable light emitter, such as a light emitting diode (LED), fluorescent light, laser, incandescent bulb, and/or other suitable light source. In some cases, the emission of light may be infrared (IR) light, in which case the light emitter will be an IR light emitter. Further, in some cases the intelligent assistant computing device may include a set of several signal emitters, and each signal emitter of the set may emit a separate instance of the position calibration signal. As will be discussed in more detail below, when the set of signal emitters have a known spatial relationship, examining the detected spatial relationship of multiple detections of the position calibration signal can aid the second intelligent assistant computing device in estimating the relative position of the first intelligent assistant computing device.

Figure 7B:
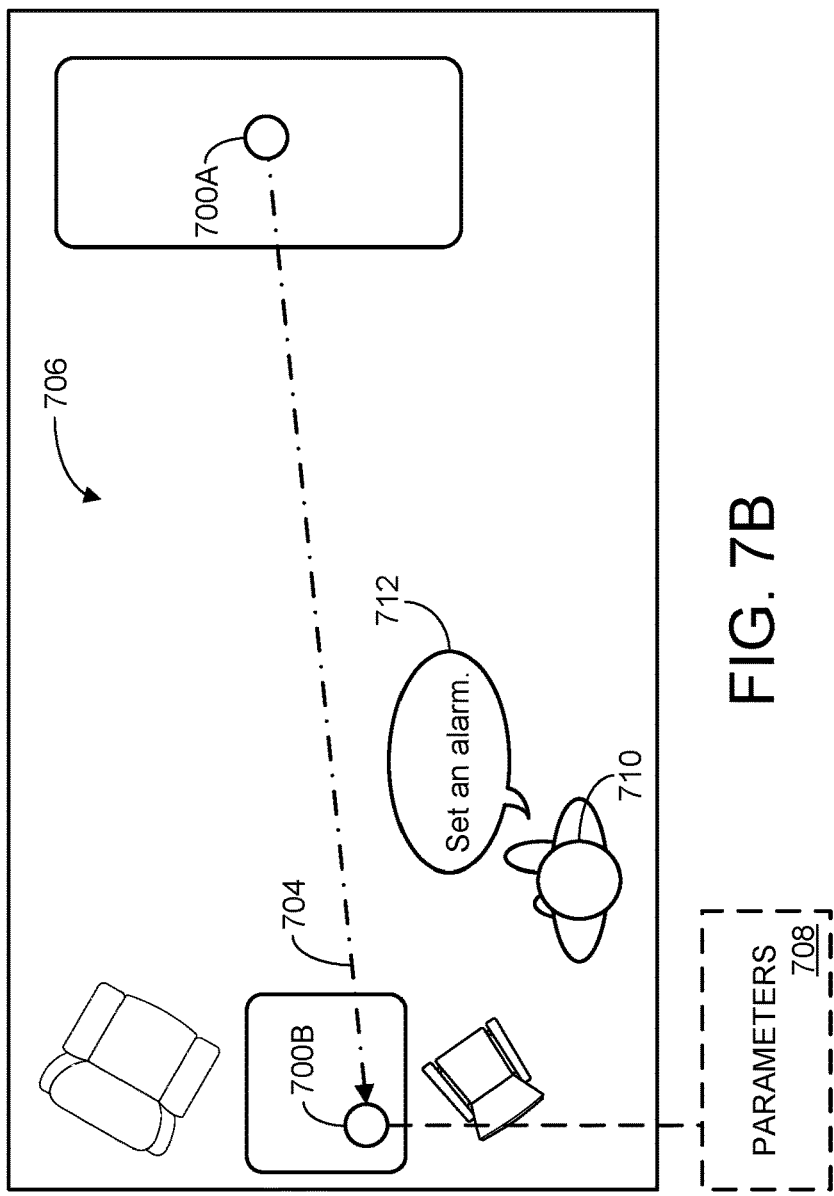
FIGS. 7A-7C illustrate emission of a position calibration signal as an emission of light.
Figure 7A:
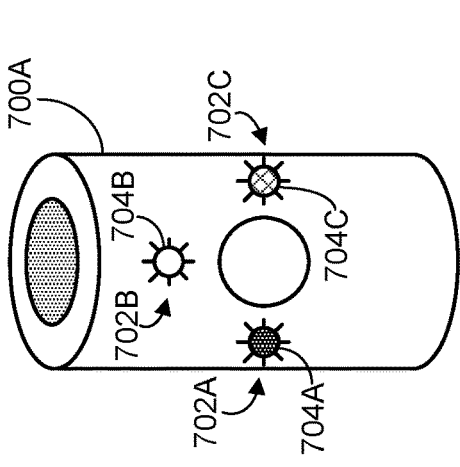

FIG. 7A illustrates an example intelligent assistant computing device 700 having a set of signal emitters 702A, 702B, and 702C. Each of the signal emitters is emitting an instance 704 of a position calibration signal, illustrated as a set of short line segments surrounding the signal emitters to indicate that the position calibration signal instances are coming out of the page. In some examples, at least one instance of the position calibration signal may be emitted differently from other instances of the position calibration signal. For example, at least one instance of the position calibration signal may be emitted with a different intensity (i.e., light that is brighter or darker), with a different wavelength, flashed at a different frequency or with a different flash pattern, etc., as compared to other position calibration signal instances. This is indicated in FIG. 7A by the different fill pattern used in each of the signal emitters 702.

FIG. 7B shows an overhead view of an example environment 706 including first intelligent assistant computing device 700A. Environment 706 also includes a second intelligent assistant computing device 700B, and shows a single instance 704 of a position calibration signal sent from the first intelligent assistant computing device to the second intelligent assistant computing device.

Returning to FIG. 6, at 604, method 600 includes, at the second intelligent assistant computing device and via one or more cameras, recording a set of parameters describing a detection of the position calibration signal. As examples, such parameters can include an intensity (e.g., brightness), wavelength, flash frequency, etc., of the position calibration signal, and/or a position at which the position calibration signal was detected relative to a FOD of a sensor (e.g., camera, light detector) of the second intelligent assistant computing device. It will be understood that these parameters are examples, and an intelligent assistant computing device may record any suitable parameters regarding a detection of a position calibration signal.

This is illustrated in FIG. 7B, in which position calibration signal 704 is detected by second intelligent assistant computing device 700B. As a result, the second intelligent assistant computing device records a set of parameters 708.

Turning again to FIG. 6, at 606, method 600 includes, based on the set of parameters, estimating relative positions of the first and second intelligent assistant computing devices. Estimating a "relative position" generally includes identifying an approximate position of one intelligent assistant computing device (e.g., the first intelligent assistant computing device) relative to the other intelligent assistant computing device. In other words, the intelligent assistant computing device may estimate that the other device is a certain distance away and at a certain angle (e.g., angle relative to a horizontal and/or vertical plane). In a different example, estimating the position of an intelligent assistant computing device may include assigning the intelligent assistant computing device coordinates relative to a real-world environment and/or a shared coordinate system.

The specific calculations performed when estimating the relative positions of the intelligent assistant computing devices will generally depend on the specific parameters recorded. In some cases, when the position calibration signal is detected at a particular position within a FOD of a sensor (e.g., defined by a sensor-relative coordinate system), the FOD-relative position can be translated into a real-world position defined relative to a real-world environment of the intelligent assistant computing device. For example, when a camera detects an emission of light, then the detected intensity can be used to confirm whether the detection corresponds to a direct line-of-sight between the two intelligent assistant computing devices or a reflection of the emission of light. If the zoom parameters and view direction of the camera are known, then the relative position of an intelligent assistant device can be inferred based on detection of a position calibration signal at a particular FOD-relative position. Such calculations may be easier and/or more accurate when multiple instances of the position calibration signal are detected. It will be understood that the relative real-world positions of the intelligent assistant computing devices may be estimated in any of a variety of suitable ways, and the specific approaches used will vary depending on the available sensors and sensor data.

In some cases, estimating the relative position of the first intelligent assistant computing device can include calculating an orientation of the first intelligent assistant computing device relative to the second. For example, when the first intelligent assistant computing device includes a set of signal emitters, each signal emitter emitting a separate instance of the position calibration signal, then the second intelligent assistant device may record multiple detections of the position calibration signal corresponding to the separate instances. An observed spatial relationship of the multiple detections can then be compared to a known spatial relationship of the signal emitters to calculate the orientation of the first intelligent assistant computing device. In an example scenario, the set of signal emitters may be arranged in a triangle. If the multiple detections are arranged in a distorted triangle, then a computer-vision transform may be used to estimate the orientation of the intelligent assistant computing device that would produce the observed distorted triangle.

It will be understood that such orientation estimation may be performed in any suitable way, using any suitable publicly-known pose estimation techniques or computer vision algorithms. As an example, orientation estimation may be performed using the solvePnP algorithm from the Open Source Computer Vision Library. This algorithm generally works by comparing the observed positions of marker points (e.g., corners of a triangle, features of a human face) in a two-dimensional image to a known three-dimensional relationship of the marker points in an arbitrary coordinate system. Specifically, the known 3D relationship of the marker points is projected onto the 2D image plane, and, provided that intrinsic properties of the camera are known, the six-degree of freedom (6DOF) pose of the object (e.g., intelligent assistant computing device) is determined. Another suitable algorithm may be the posest algorithm, provided under an open source license by the Institute of Computer Science of the Foundation for Research and Technology—Hellas.

Figure 7C:
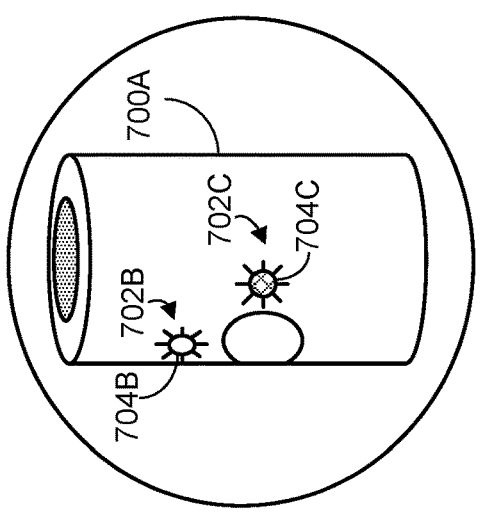

This is illustrated in FIG. 7C. In this example, the known spatial relationship of the signal emitters is a triangle. However, in FIG. 7C, only two instances of the position calibration signal are visible, with the third instance being occluded by the side of the intelligent assistant computing device. Based on the detected instances, the second intelligent assistant computing device can infer that the first intelligent assistant computing device is rotated clockwise, and calculate the angle of this rotation.

Returning to FIG. 6, at 608, method 600 includes receiving a natural language input from a human user in the environment of the first and second intelligent assistant computing devices. This is illustrated in FIG. 7B, in which a human user 710 provides a natural language input 712 (i.e., requesting than an alarm be set). Natural language input 712 may be received by either or both of first intelligent assistant computing device 700A and second intelligent assistant computing device 700B, for instance via one or more microphones of the intelligent assistant computing devices.

Returning to FIG. 6, at 610, method 600 includes, based on the relative positions of the first and second intelligent assistant computing devices, determining which of the first and second intelligent assistant computing devices is closer to a position of the human user. In FIG. 7B, second intelligent assistant device 700B is closer to the position of human user 710 than first intelligent assistant device 700A.

It will be understood that identifying the position of the human user may be done in any suitable way. In some examples, the position of the human user may be determined by an entity tracker of an intelligent assistant computing device, using any or all of the entity tracking techniques described above. Furthermore, the position of the human user may be compared to the positions of the intelligent assistant computing devices in any suitable way. In some examples, each of these positions may be expressed relative to the environment (e.g., using an environment-relative coordinate system), in which case it may be relatively trivial to calculate a shortest Euclidean distance between the positions of the human user and each of the intelligent assistant computing devices. When the positions are not all expressed relative to the environment, then the closest device to the human user may be identified in another suitable way, for instance by comparing the amplitude of the natural language input detected at each of the intelligent assistant computing devices, or identifying which of the intelligent assistant computing devices has a better view of the human user (e.g., via a camera). The decision of which of the intelligent assistant computing devices is closer to the position of the human user may be made by any suitable computing device, including either or both of the intelligent assistant computing devices, another computing device in the environment, a remote server, etc.

Returning to FIG. 6, at 612, method 600 includes responding to the natural language input via the closer intelligent assistant computing device. In the example of FIG. 7B, upon determining that second intelligent assistant computing device 700B is the closer intelligent assistant computing device, then device 700B may respond to the natural language input. This may include, for example, asking the user what time the alarm should be set for, confirming that the alarm has been set, and/or providing other suitable responses based on the nature of the natural language input. Notably, while second intelligent assistant device 700B is responding to the natural language input, first intelligent assistant device 700A, as well as other intelligent assistant computing devices in the environment, may remain substantially inactive. In other words, such devices may refrain from unnecessarily expending electrical and/or processing power in attempting to respond to the natural language input. It will be understood that such devices may or may not continue to perform other functions besides responding to natural language inputs while inactive.

In some scenarios, emission of a position calibration signal may be used for purposes in addition to or instead of determining the position of an intelligent assistant computing device. For example, emission of a position calibration signal may be used to determine information regarding the positions of one or more surfaces in an environment of the intelligent assistant computing devices. After one intelligent assistant computing device emits a position calibration signal, the position calibration signal may in some cases reflect off one or more reflection surfaces in the environment prior to being detected by the other intelligent assistant computing device. Based on analysis of the detected position calibration signal, information regarding the path taken by the position calibration signal can be derived, thereby providing at least some information regarding the layout of the environment. When a plurality of instances of the position calibration signal are detected, each having reflected off a different reflection surface, the intelligent assistant computing device may have sufficient information to estimate a layout of the environment. Further, other information, such as camera images, may be considered together with position calibration signal information to model an environment. Modelling the environment can further improve the ability of the intelligent assistant computing device to provide intelligent assistance, for instance by allowing the intelligent assistant computing device to identify points of entry/egress, notable furniture/appliances, better understand movements of human users throughout the environment, etc.

Figure 8A:
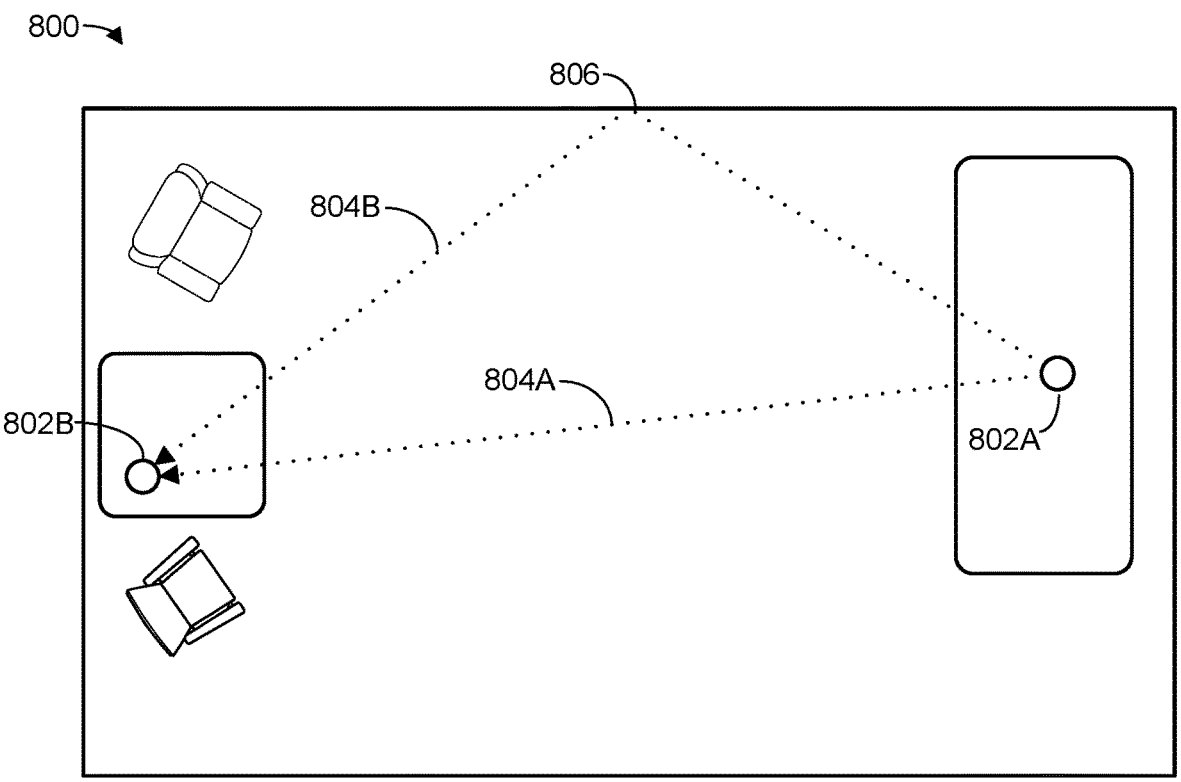
FIGS. 8A and 8B illustrate reflection of a position calibration signal off reflection surfaces in an environment.
Figure 8B:
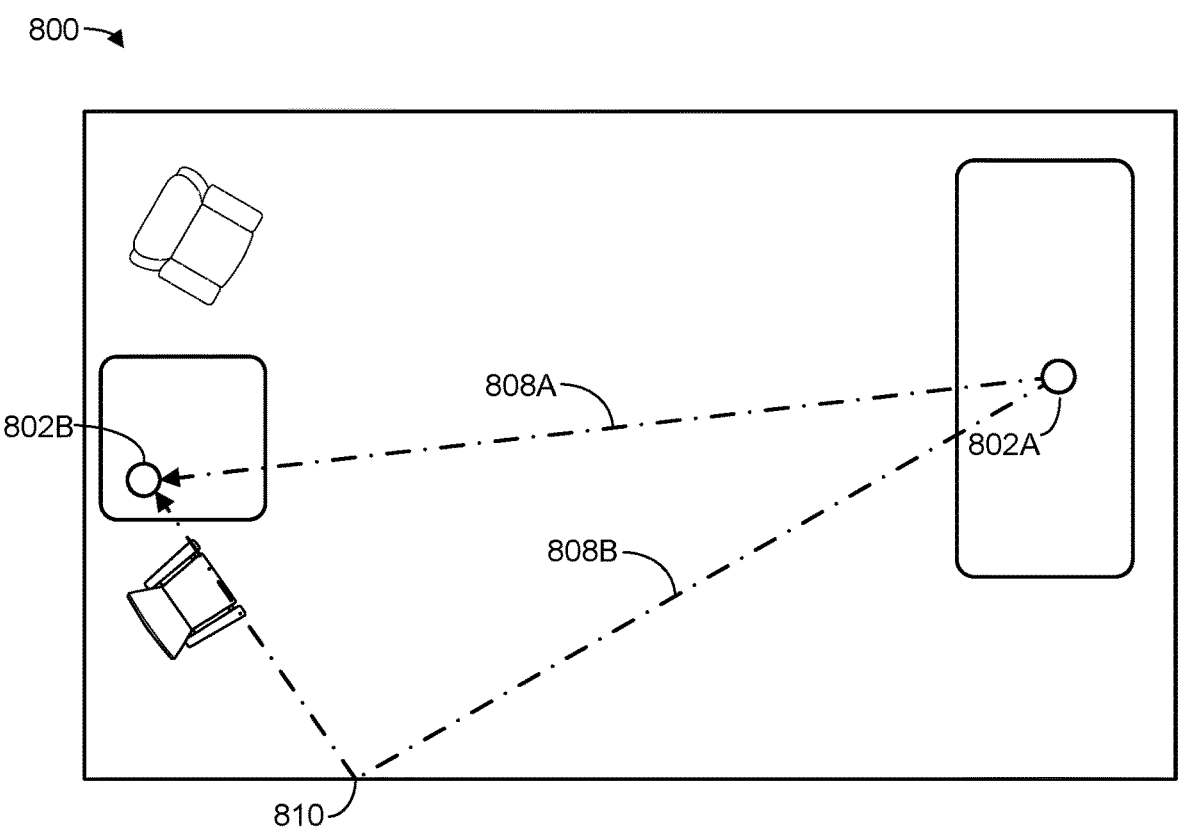

Reflection of a position calibration signal off a reflection surface in an environment is schematically illustrated in FIGS. 8A and 8B. FIG. 8A shows an example environment 800 including a first intelligent assistant computing device 802A emitting a position calibration signal 804. In FIG. 8B, the position calibration signal is an emission of sound, which may radiate in a plurality of directions around the intelligent assistant computing device after emission. For purposes of illustration, two emissions of sound 804A and 804B are shown in FIG. 8B, each traveling in different directions. It will be understood that these two emissions are slices of a single three-dimensional sound waveform emitted by a speaker of the first intelligent assistant computing device, and this three-dimensional waveform may exhibit complex reflections and interactions not shown in FIG. 8A. Nonetheless, emissions of sound 804A and 804B will be described as separate instances of a position calibration signal, much as if they had been emitted in different directions by two highly-directional speakers.

The two emissions of sound are detected by a second intelligent assistant computing device 804B. While emission of sound 804A takes a direct path between the first and second intelligent assistant computing devices, emission of sound 804B reflects off reflection surface 806 en route. In other words, second emission of sound 804B may correspond to an echo of the original emission of sound, reaching the second intelligent assistant device at a measurable length of time after the initial detection of the position calibration signal. The second intelligent assistant computing device will therefore record a first signal detection time of a first detection of the emission of sound (i.e., emission of sound 804A), and a second detection of the emission of sound (i.e., emission of sound 804B), the second detection corresponding to a reflection of the emission of sound off a reflection surface in the environment. The second intelligent assistant computing device may then compare the time-of-flight for the second detection of the emission of sound to the known propagation speed of sound to calculate the total distance traveled by the second emission of sound, as described above with respect to FIG. 4. This corresponds to the cumulative distance between a) the second intelligent assistant computing device and the reflection surface, and b) the reflection surface and the first intelligent assistant computing device. Notably this calculation only applies to emissions of sound that reflect off a single reflection surface, but could be expanded to account for multiple reflections.

As discussed above, an emission of sound from an intelligent assistant computing device will typically take the form of a complex three-dimensional sound waveform, portions of which may end up reflecting off any or all of the surfaces in the local environment prior to being detected by the second intelligent assistant computing device. Because the emission time of the emission of sound is known, the multiple detections of the emission of sound can be used as the basis for performing echolocation using suitable sound processing techniques. In this manner, based on a plurality of detections of the emission of sound, the second intelligent assistant computing device and/or another suitable computing device can calculate a plurality of distances between the first intelligent assistant computing devices and a plurality of reflection surfaces in the environment. This information may be useable to estimate a layout of the environment, which can present advantages with respect to intelligent assistance as described above.

Reflections of the position calibration signal may also be observed when the position calibration signal is an emission of light. This is illustrated in FIG. 8B, which again shows intelligent assistant computing devices 802A and 802B in environment 800. In FIG. 8B, however, first intelligent assistant computing device 802A has emitted two different emissions of light 808A and 808B. The second emission of light has reflected off a reflection surface 810 prior to detection by the second intelligent assistant computing device. Depending on the reflectivity of reflection surface 810, the second emission of light will likely be detected by the second intelligent assistant computing device with a lower intensity than the first intelligent assistant computing device. The second intelligent computing device may compare these intensities to confirm that the second emission of light corresponds to a reflection.

As discussed above with respect to FIG. 6, the real-world location of the source of an emission of light may be estimated based on the position at which the emission of light is detected (e.g., relative to the FOD of a sensor, such as a camera). Accordingly, in the case of second emission of light 808B, based on the position at which the emission of light was detected by a camera of the second intelligent assistant computing device, and a determination (e.g., based on intensity) that the second emission of light corresponds to a reflection, then the second intelligent assistant computing device and/or other suitable devices may calculate the relative position of the reflection surface off of which the second emission of light reflected.

FIG. 9 illustrates an example method for position calibration based on presence of a human user. As with other methods described herein, method 900 may be implemented on relatively stationary "all-in-one" intelligent assistant computing devices, such as device 104 shown in FIG. 1. However, it will be understood that method 900 may be implemented on any computer hardware suitable for receiving, processing, and responding to natural language inputs. In some examples, method 900 may be implemented on computing system 1300 described below with respect to FIG. 13.

At 902, method 900 includes, at a first intelligent assistant computing device, detecting presence of a human user at a first detection position within a field-of-detection (FOD) of the first intelligent assistant computing device. As an example, the first intelligent assistant computing device may include one or more cameras, each having a FOD of an environment of the intelligent assistant computing device. The human user may be detected at a particular position (e.g., pixel position) within the FOD of the camera, corresponding to the first detection position.

Figure 10A:
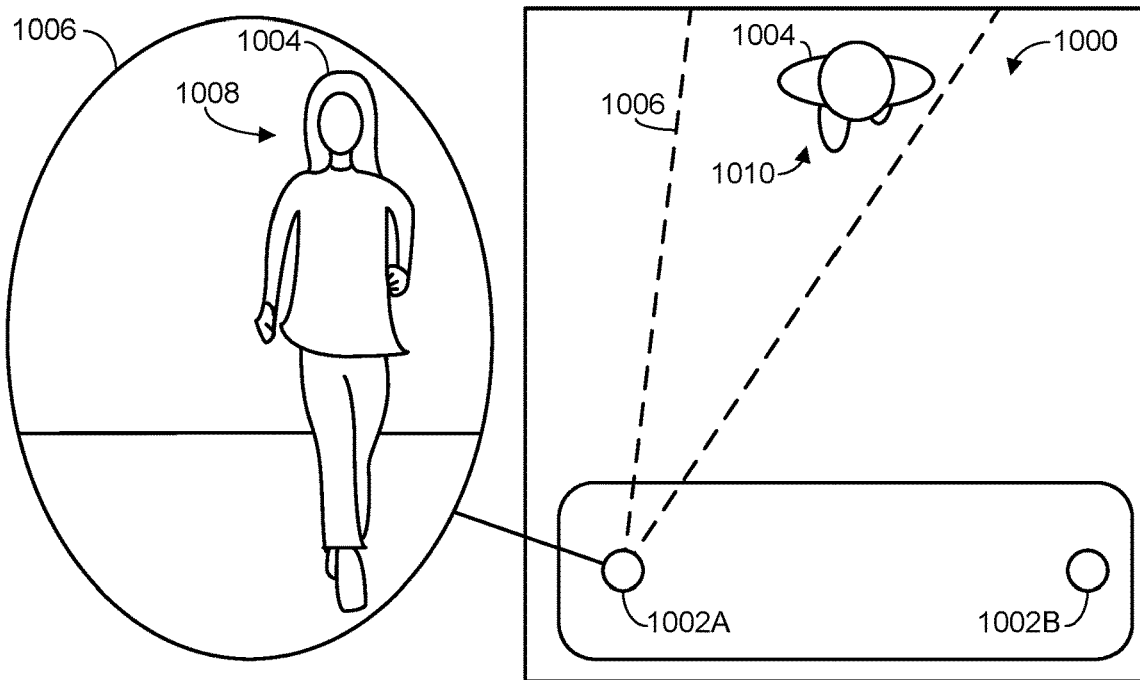
FIGS. 10A-10C schematically illustrate position calibration based on presence of a human user.

This is illustrated in FIG. 10A, which shows an overhead view of an example environment 1000, including a first intelligent assistant computing device 1002A and a second intelligent assistant computing device 1002B. Environment 1000 also includes a human user 1004, visible within a FOD 1006 of a camera of first intelligent assistant computing device 1002A. FOD 1006 is shown both in the overhead view of environment 1000, as well as from the perspective of the first intelligent assistant computing device looking toward the human user. As shown, human user 1008 has been detected at a first detection position 1008 relative to FOD 1006. As discussed above, first detection position 1008 may, for example, be defined relative to a grid of pixels of the camera or an image captured by the camera.

Returning to FIG. 9, At 904, method 900 includes localizing the human user to a real-world position relative to an environment of the first intelligent assistant computing device corresponding to the first detection position. This may be done in a variety of suitable ways (e.g., range finding, depth camera, image analysis). FIG. 10A shows that the first detection position has been localized to a real-world position relative to environment 1000, shown as position 1010 within the overhead view of environment 1000.

Figure 10B:
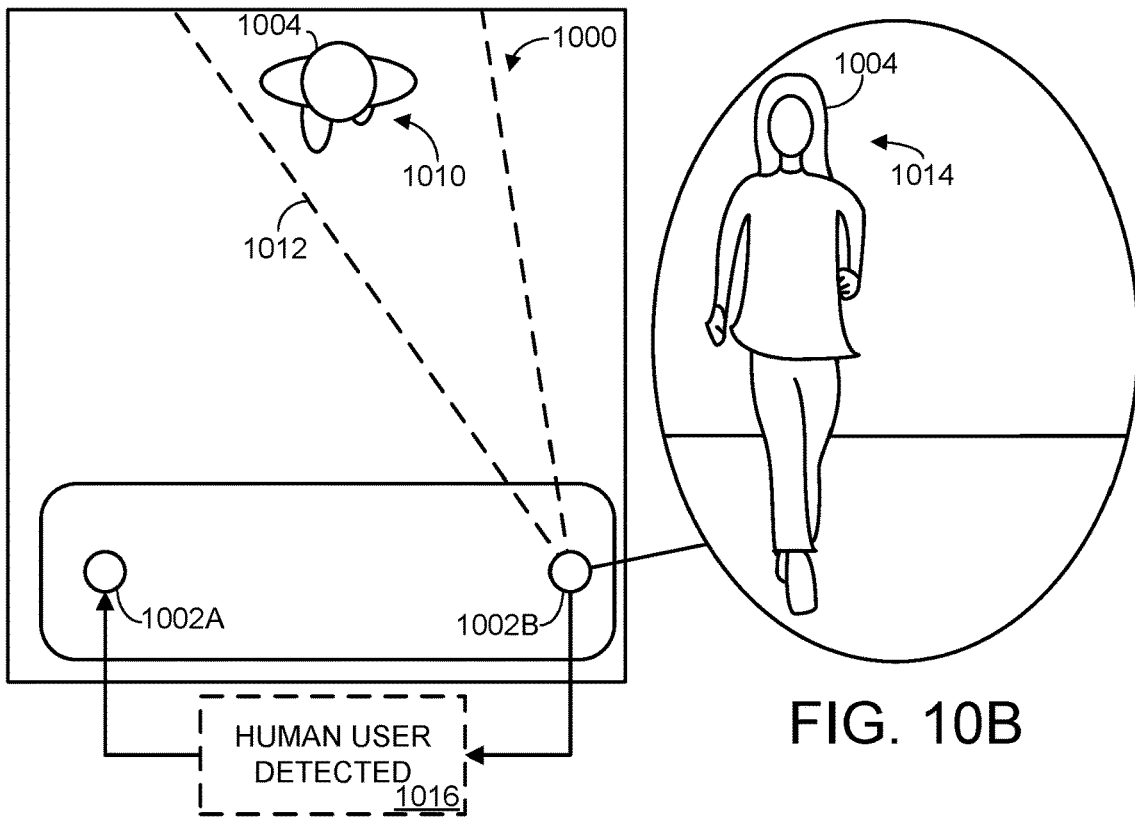
Figure 10C:
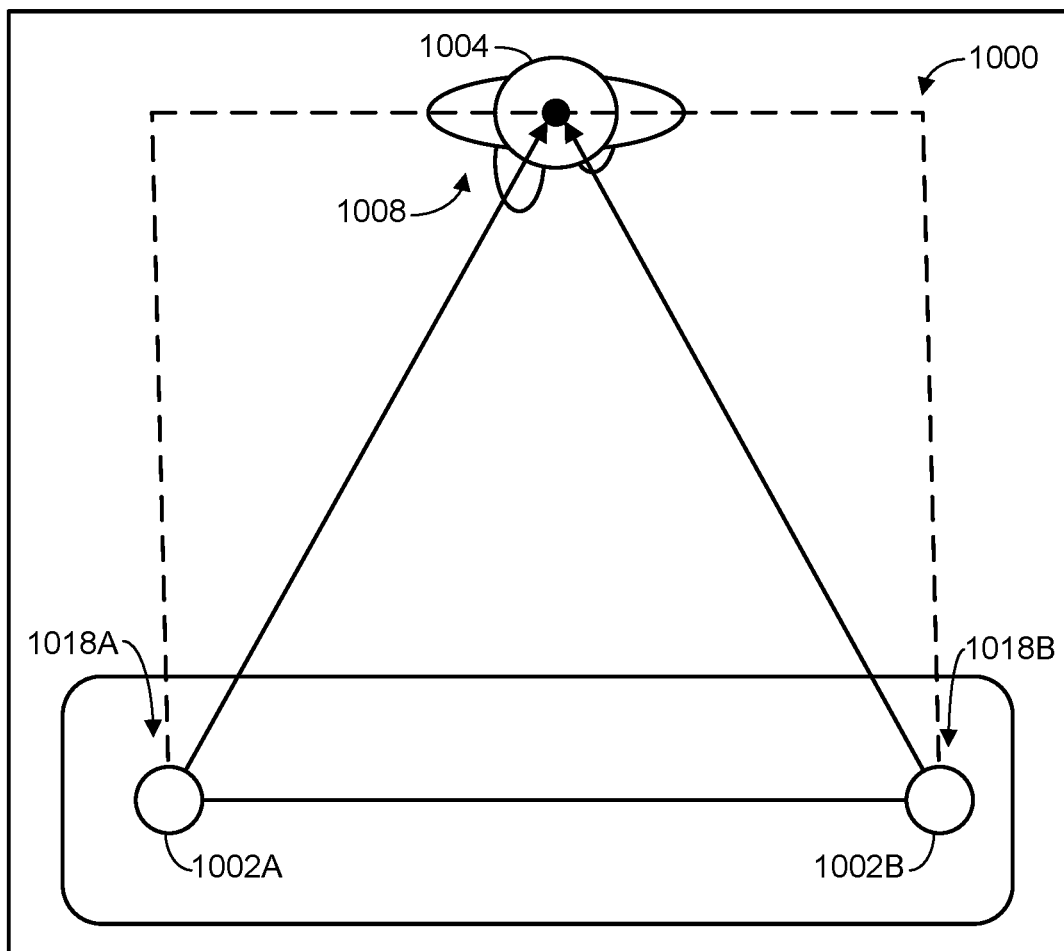

Returning to FIG. 9, at 906, method 900 includes, via a wireless computer network, receiving, from a second intelligent assistant computing device, an indication that the second intelligent assistant computing device detected the human user at a second detection position within a FOD of the second intelligent assistant computing device, the second detection position also corresponding to the real-world position. This is illustrated in FIG. 10B, which again shows an overhead view of environment 1000. In FIG. 10B, human user 1004 has not moved from real-world position 1010, and is visible in a FOD 1012 of second intelligent assistant computing device 1012, again shown in both the overhead view of environment 1000 and on its own from the perspective of second intelligent assistant computing device 1002B. Within FOD 1012, human user 1004 has been detected at a second detection position 1004, corresponding to real-world position 1010. An indication 1016 of the detection of human user 1004 is transmitted from the second intelligent assistant computing device to the first via a wireless computer network.

Returning to FIG. 9, at 908, method 900 includes, using the real-world position of the human user as a landmark, estimating real-world positions for each of the first and second intelligent assistant computing devices. For example, upon detecting the human user at a detection position within its FOD, each intelligent assistant computing device may estimate its own position relative to the human user, though still have no information regarding the position of the other intelligent assistant computing device. However, when the human user is detected at different FOD-relative detection positions though remains at the same real-world position, the position of the human user may be treated as a fixed point or landmark. The positions of both intelligent assistant computing devices may then be estimated relative to the real-world position of the human user, and therefore the real-world environment, by any device having sufficient information regarding the first and second detection positions of the human user. Such a device can include either or both of the intelligent assistant computing devices (e.g., the first intelligent assistant computing device upon receiving indication 1016), or another suitable device, such as a remote server.

In some cases, after position calibration is complete, the position of an intelligent assistant computing device may change, either through accidental movement or deliberate repositioning by a human user. When this occurs, the position information obtained via position calibration may be rendered out-of-date, which can diminish or negate the advantages achieved through performing position calibration in the first place.

Accordingly, in some cases, upon detecting a change in position of an intelligent assistant computing device, an updated distance between the intelligent assistant computing devices may be calculated. This may be done in any of a variety of suitable ways, including updating the distance based on changes detected in a FOD of a camera, updating the distance based on data output by a motion sensor, simply repeating any or all of the position calibration steps described above, and/or other suitable processes.

Figure 11A:
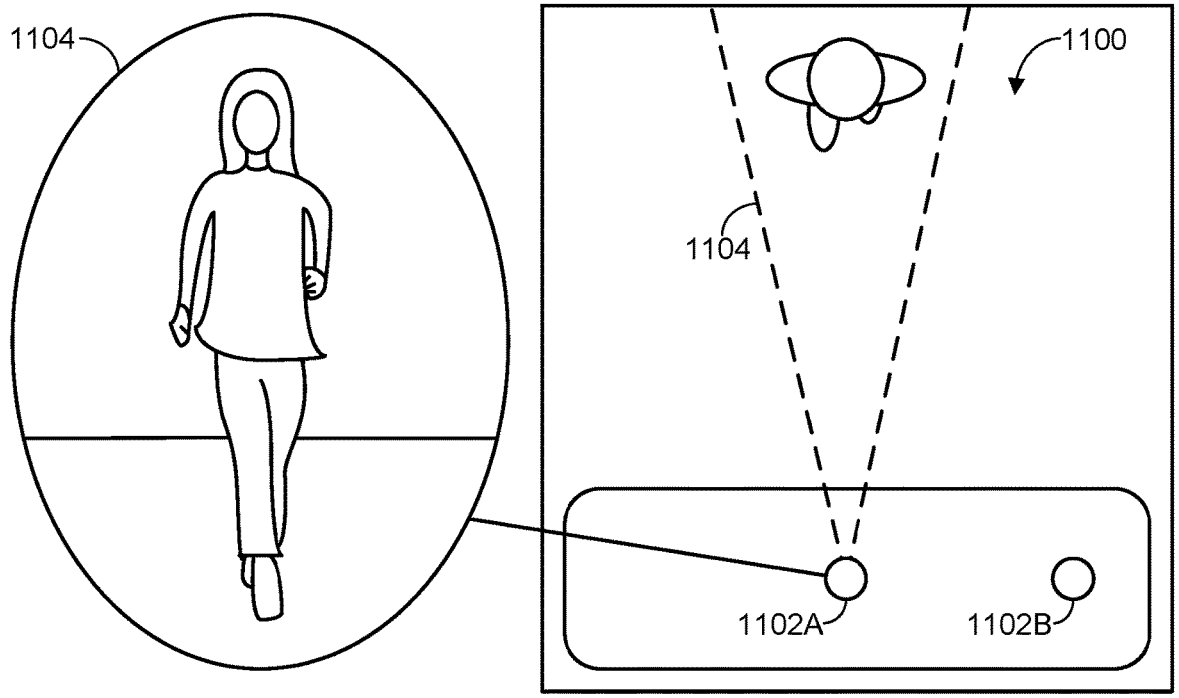
FIGS. 11A and 11B schematically illustrate position correction of an intelligent assistant computing device based a change in images captured by a camera.

FIG. 11A shows an overhead view of another example environment 1100, including two intelligent assistant computing devices 1102A and 1102B. In the example of FIG. 11A, any or all of the position calibration steps described above have been performed, such that first intelligent device 1102A has information regarding its distance from and/or position relative to second intelligent assistant computing device 1102B. First intelligent assistant computing device 1102A has a FOD 1104 of environment 1100, shown both in overhead view 1100 and on its own from the perspective of first intelligent assistant computing device 1102A.

Figure 11B:
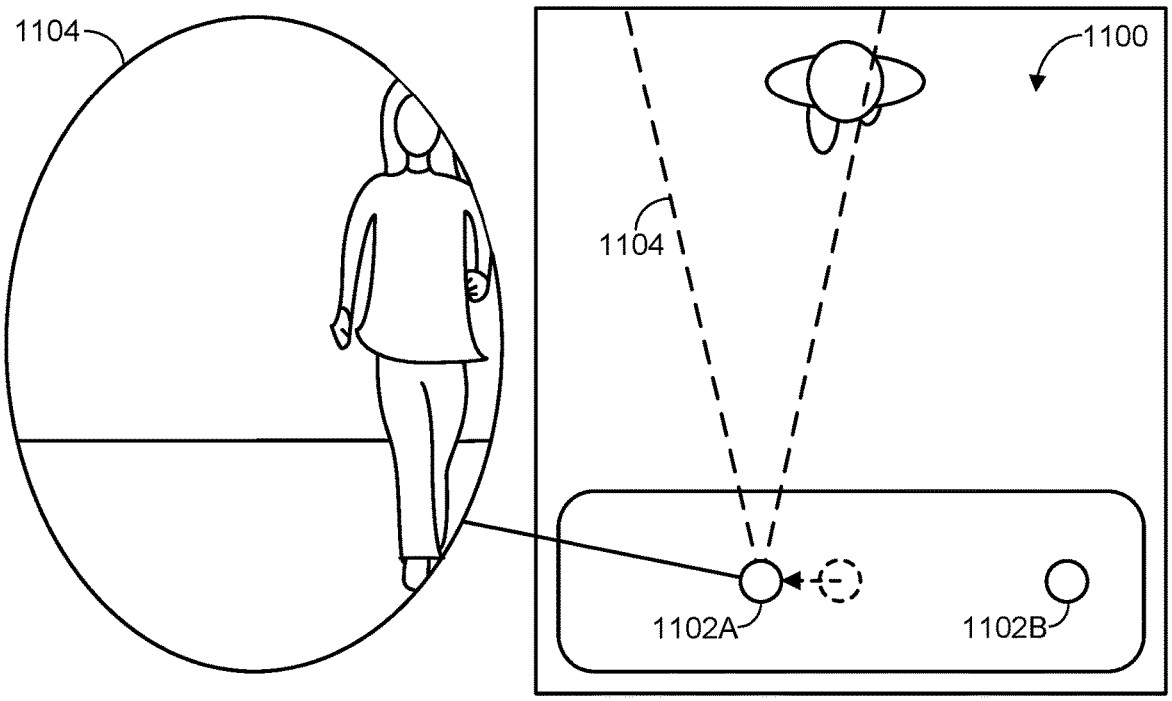

In FIG. 11B, first intelligent assistant computing device 1102A has detected a change in its position. This is illustrated by the dashed circle and arrow shown in FIG. 11B, indicating the change in position of the device. This change in position may be inferred from the change in images visible in FOD 1104. Specifically, the position of the human user visible in FOD 1104 has changed, though the real-world position of the human user has not. This may be inferred, for example, by observing that all images in the FOD shifted by the same or similar amounts (accounting for parallax). Based on this detected change in imagery, the first intelligent assistant computing device may calculate an updated distance between the first and second intelligent assistant computing devices, for example by applying a computer vision transform to imagery visible in the updated FOD to estimate its own change in position.

Additionally, or alternatively, the change in position of the first intelligent assistant computing device may be detected by one or more motion sensors of the first intelligent assistant computing device (e.g., accelerometers, magnetometers, gyroscopes, inertial measurement units). The change in position of the first intelligent assistant computing device may then be calculated based on data output by the one or more motion sensors, and such data may be processed, fused, combined, etc., in any suitable way.

Figure 12:
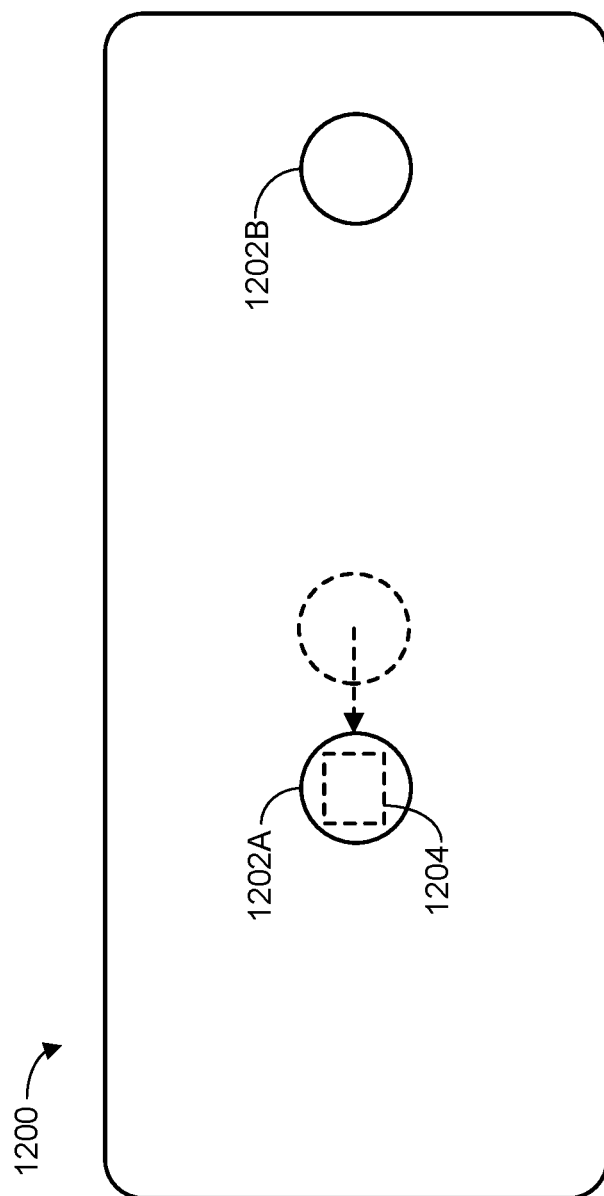
FIG. 12 schematically illustrates position correction of an intelligent assistant computing device based on motion sensors of the intelligent assistant computing device.

This is schematically illustrated in FIG. 12, which shows an overhead view of an example environment 1200 including a first intelligent assistant computing device 1202A and a second intelligent assistant computing device 1202B. In the example of FIG. 12, any or all of the position calibration steps described above have been performed, such that first intelligent device 1202A has information regarding its distance from and/or position relative to second intelligent assistant computing device 1202B. However, the position of the first intelligent assistant computing device has changed, illustrated by the dashed circle and arrow shown in FIG. 12. This change may be detected by a motion sensor 1204 of the first intelligent assistant computing device, which may output data useable for calculating the distance and/or direction of the detected change in position, as described above.

Furthermore, additionally or alternatively to the processes described above, upon detecting a change in its position, the first intelligent assistant computing device may instruct the second intelligent assistant computing device to output a new position calibration signal. This may result in, for example, steps of methods 400 and/or 600 described above being performed, allowing the first intelligent assistant computing device to calculate an updated distance from and/or position relative to the second intelligent assistant computing device.

Though the above description focused on calculating distances between and/or relative positions of pairs of intelligent assistant computing devices, it will be understood that the position calibration techniques described herein may be applied to any arbitrary number of intelligent assistant computing devices. For example, some implementations may feature three, four, five, or more intelligent assistant computing devices. When more than two intelligent assistant computing devices are used, two different position calibration signals may be received by the same intelligent assistant computing device, potentially allowing the device to more accurately triangulate its distance from and/or position relative to the other intelligent assistant devices. Furthermore, though the position calibration techniques described above were discussed separately (e.g., in methods 400, 600, and 900), it will be understood that a single intelligent assistant computing device may utilize any or all of the described techniques, either in sequence or in parallel, and/or use position calibration techniques not explicitly described herein.

In some embodiments, the methods and processes described herein may be tied to a computing system of one or more computing devices. In particular, such methods and processes may be implemented as a computer-application program or service, an application-programming interface (API), a library, and/or other computer-program product.

Figure 13:
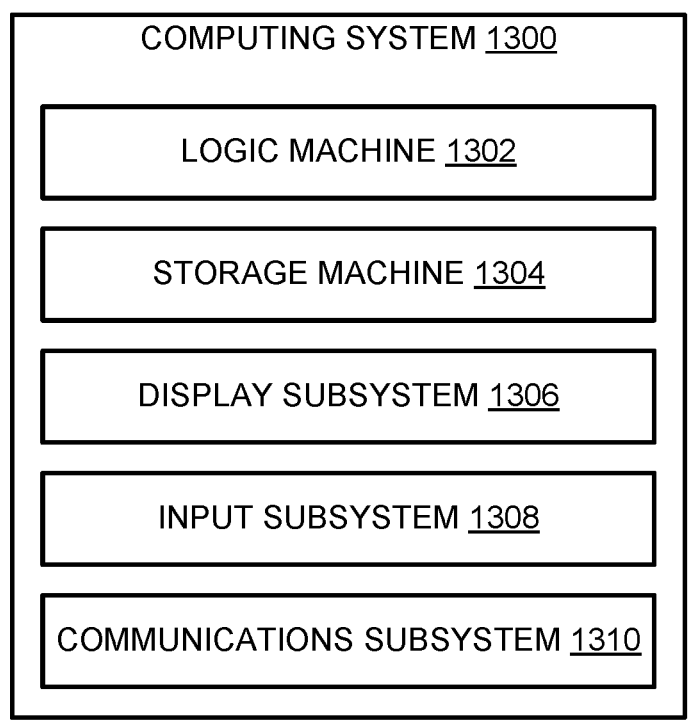
FIG. 13 schematically illustrates an example computing system.

FIG. 13 schematically shows a non-limiting embodiment of a computing system 1300 that can enact one or more of the methods and processes described above. Computing system 1300 is shown in simplified form. Computing system 1300 may take the form of one or more personal computers, server computers, tablet computers, home-entertainment computers, network computing devices, gaming devices, mobile computing devices, mobile communication devices (e.g., smart phone), and/or other computing devices.

Computing system 1300 includes a logic machine 1302 and a storage machine 1304. Computing system 1300 may optionally include a display subsystem 1306, input subsystem 1308, communication subsystem 1310, and/or other components not shown in FIG. 13.

Logic machine 1302 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 1304 includes one or more physical devices configured to hold instructions executable by the logic machine to implement the methods and processes described herein. When such methods and processes are implemented, the state of storage machine 1304 may be transformed—e.g., to hold different data.

Storage machine 1304 may include removable and/or built-in devices. Storage machine 1304 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 1304 may include volatile, nonvolatile, dynamic, static, read/write, read-only, random-access, sequential-access, location-addressable, file-addressable, and/or content-addressable devices.

It will be appreciated that storage machine 1304 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 1302 and storage machine 1304 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 1300 implemented to perform a particular function. In some cases, a module, program, or engine may be instantiated via logic machine 1302 executing instructions held by storage machine 1304. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, display subsystem 1306 may be used to present a visual representation of data held by storage machine 1304. This visual representation may take the form of a graphical user interface (GUI). As the herein described methods and processes change the data held by the storage machine, and thus transform the state of the storage machine, the state of display subsystem 1306 may likewise be transformed to visually represent changes in the underlying data. Display subsystem 1306 may include one or more display devices utilizing virtually any type of technology. Such display devices may be combined with logic machine 1302 and/or storage machine 1304 in a shared enclosure, or such display devices may be peripheral display devices.

When included, input subsystem 1308 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 1310 may be configured to communicatively couple computing system 1300 with one or more other computing devices. Communication subsystem 1310 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1300 to send and/or receive messages to and/or from other devices via a network such as the Internet.

In an example, a method comprises: at a first intelligent assistant computing device configured to receive and respond to natural language inputs provided by human users, syncing to a reference clock of a wireless computer network, the reference clock being supported by a second intelligent assistant computing device communicatively coupled to the first intelligent assistant computing device via the wireless computer network; receiving a communication sent by the second intelligent assistant computing device over the wireless computer network, the communication indicating a signal emission time at which the second intelligent assistant computing device emitted a position calibration signal, the signal emission time being defined relative to the reference clock; recording a signal detection time at which the position calibration signal was detected by the first intelligent assistant computing device, the signal detection time being defined relative to the reference clock; and based at least on a difference between the signal emission time and the signal detection time and a known propagation speed of the position calibration signal, calculating a distance between the first intelligent assistant computing device and the second intelligent assistant computing device. In this example or any other example, the position calibration signal is an emission of sound. In this example or any other example, the emission of sound includes a plurality of different frequencies, one or more of the plurality of frequencies being an ultrasonic frequency. In this example or any other example, the method further comprises recording an amplitude of the detected position calibration signal, and calculating the distance further includes comparing the recorded amplitude to a known emission amplitude of the position calibration signal. In this example or any other example, the first intelligent assistant computing device detects the emission of sound via a beamforming microphone array, and the method further comprises recording a direction from which the emission of sound was detected. In this example or any other example, recording the signal detection time includes recording a first signal detection time of a first detection of the emission of sound and a second signal detection time of a second detection of the emission of sound, the second detection of the emission of sound corresponding to a reflection of the emission of sound off a reflection surface in an environment of the first intelligent assistant computing device, and the method further comprises calculating a cumulative distance between a) the second intelligent assistant computing device and the reflection surface, and b) the reflection surface and the first intelligent assistant computing device. In this example or any other example, the method further comprises calculating a plurality of distances between the first intelligent assistant computing device and a plurality of reflection surfaces in the environment based on a plurality of detections of the emission of sound, and estimating a layout of the environment based on the plurality of distances. In this example or any other example, the method further comprises, upon detecting a change in position of the first intelligent assistant computing device, calculating an updated distance between the first and second intelligent assistant computing devices. In this example or any other example, the change in position of the first intelligent assistant computing device is detected by one or more motion sensors of the first intelligent assistant computing device, and the updated distance is calculated based on data output by the one or more motion sensors. In this example or any other example, the first intelligent assistant computing device includes a camera, detecting the change in position of the first intelligent assistant computing device includes detecting a change in images captured by the camera, and the updated distance is calculated based on the detected change. In this example or any other example, the method further comprises, upon detecting the change in position of the first intelligent assistant computing device, instructing the second intelligent assistant computing device to emit a new position calibration signal. In this example or any other example, the method further comprises: detecting a natural language input provided by a human user; based on the distance between the first and second intelligent assistant computing devices, determining which of the first and second intelligent assistant computing devices is closer to a position of the human user; and responding to the natural language input via the closer intelligent assistant computing device.

In an example, a method comprises: at a first intelligent assistant computing device, emitting a position calibration signal via a signal emitter, the position calibration signal being an emission of light; at a second intelligent assistant computing device, via one or more cameras, recording a set of parameters describing a detection of the position calibration signal; based on the set of parameters describing the detection, estimating relative positions of the first and second intelligent assistant computing devices; receiving a natural language input from a human user in an environment of the first and second intelligent assistant computing devices; based on the relative positions of the first and second intelligent assistant computing devices, determining which of the first and second intelligent assistant computing devices is closer to a position of the human user; and responding to the natural language input via the closer intelligent assistant computing device. In this example or any other example, the signal emitter is an infrared (IR) light emitter, and the emission of light is an emission of IR light. In this example or any other example, the first intelligent assistant computing device includes a set of signal emitters having a known spatial relationship, emitting the position calibration signal includes emitting a separate instance of the position calibration signal from each of the set of signal emitters, the second intelligent assistant computing device records multiple detections of the position calibration signal corresponding to separate instances of the position calibration signal, and the method further comprises, based on comparing a spatial relationship of the multiple detections to the known spatial relationship of the set of signal emitters, calculating an orientation of the first intelligent assistant computing device relative to the second intelligent assistant computing device. In this example or any other example, emitting the position calibration signal includes emitting at least one instance of the position calibration signal differently from other instances of the position calibration signal. In this example or any other example, the method further comprises recording a set of parameters describing a second detection of the position calibration signal corresponding to a reflection of the position calibration signal off a reflection surface in the environment, and, based on the set of parameters describing the second detection, estimating a relative position of the reflection surface.

In an example, a method comprises: at a first intelligent assistant computing device, detecting presence of a human user at a first detection position within a field-of-detection (FOD) of the first intelligent assistant computing device; localizing the human user to a real-world position relative to an environment of the first intelligent assistant computing device corresponding to the first detection position; via a wireless computer network, receiving, from a second intelligent assistant computing device, an indication that the second intelligent assistant computing device detected the human user at a second detection position within a FOD of the second intelligent assistant computing device, the second detection position also corresponding to the real-world position; and using the real-world position of the human user as a landmark, estimating real-world positions for each of the first and second intelligent assistant computing devices. In this example or any other example, the method further comprises: detecting a natural language input provided by the human user; comparing the real-world positions of the first and second intelligent assistant computing devices to the real-world position of the human user to identify which of the first and second intelligent assistant computing devices are closer to the human user; and responding to the natural language input via the closer intelligent assistant computing device. In this example or any other example, the method further comprises, upon detecting a change in position of the first intelligent assistant computing device, calculating an updated distance between the first and second intelligent assistant computing devices.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method, comprising:
   at a first intelligent assistant computing device configured to receive and respond to natural language inputs provided by human users, syncing to a reference clock of a wireless computer network, the reference clock being supported by a second intelligent assistant computing device communicatively coupled to the first intelligent assistant computing device via the wireless computer network;
   receiving a communication sent by the second intelligent assistant computing device over the wireless computer network, the communication indicating a signal emission time at which the second intelligent assistant computing device emitted a position calibration signal, the signal emission time being defined relative to the reference clock;
   recording a signal detection time at which the position calibration signal was detected by the first intelligent assistant computing device, the signal detection time being defined relative to the reference clock; and
   based at least on a difference between the signal emission time and the signal detection time and a known propagation speed of the position calibration signal, calculating a distance between the first intelligent assistant computing device and the second intelligent assistant computing device.

2. The method of claim 1, where the position calibration signal is an emission of sound.

3. The method of claim 2, where the emission of sound includes a plurality of different frequencies, one or more of the plurality of frequencies being an ultrasonic frequency.

4. The method of claim 2, further comprising recording an amplitude of the detected position calibration signal, and where calculating the distance further includes comparing the recorded amplitude to a known emission amplitude of the position calibration signal.

5. The method of claim 2, where the first intelligent assistant computing device detects the emission of sound via a beamforming microphone array, the method further comprises recording a direction from which the emission of sound was detected.

6. The method of claim 2, where recording the signal detection time includes recording a first signal detection time of a first detection of the emission of sound and a second signal detection time of a second detection of the emission of sound, the second detection of the emission of sound corresponding to a reflection of the emission of sound off a reflection surface in an environment of the first intelligent assistant computing device, the method further comprises calculating a cumulative distance between a) the second intelligent assistant computing device and the reflection surface, and b) the reflection surface and the first intelligent assistant computing device.

7. The method of claim 6, further comprising calculating a plurality of distances between the first intelligent assistant computing device and a plurality of reflection surfaces in the environment based on a plurality of detections of the emission of sound, and estimating a layout of the environment based on the plurality of distances.

8. The method of claim 1, further comprising, upon detecting a change in position of the first intelligent assistant computing device, calculating an updated distance between the first and second intelligent assistant computing devices.

9. The method of claim 8, where the change in position of the first intelligent assistant computing device is detected by one or more motion sensors of the first intelligent assistant computing device, and the updated distance is calculated based on data output by the one or more motion sensors.

10. The method of claim 8, where the first intelligent assistant computing device includes a camera, detecting the change in position of the first intelligent assistant computing device includes detecting a change in images captured by the camera, and the updated distance is calculated based on the detected change.

11. The method of claim 8, further comprising, upon detecting the change in position of the first intelligent assistant computing device, instructing the second intelligent assistant computing device to emit a new position calibration signal.

12. The method of claim 1, further comprising:
  detecting a natural language input provided by a human user;
  based on the distance between the first and second intelligent assistant computing devices, determining which of the first and second intelligent assistant computing devices is closer to a position of the human user; and
  responding to the natural language input via the closer intelligent assistant computing device.

13. A method, comprising:
  at a first intelligent assistant computing device, emitting a position calibration signal via a signal emitter, the position calibration signal being an emission of light;
  at a second intelligent assistant computing device, via one or more cameras, recording a set of parameters describing a detection of the position calibration signal;
  based on the set of parameters describing the detection, estimating relative positions of the first and second intelligent assistant computing devices;
  receiving a natural language input from a human user in an environment of the first and second intelligent assistant computing devices;
  based on the relative positions of the first and second intelligent assistant computing devices, determining which of the first and second intelligent assistant computing devices is closer to a position of the human user; and
  responding to the natural language input via the closer intelligent assistant computing device.

14. The method of claim 13, where the signal emitter is an infrared (IR) light emitter, and the emission of light is an emission of IR light.

15. The method of claim 13, where the first intelligent assistant computing device includes a set of signal emitters having a known spatial relationship, emitting the position calibration signal includes emitting a separate instance of the position calibration signal from each of the set of signal emitters and the second intelligent assistant computing device records multiple detections of the position calibration signal corresponding to separate instances of the position calibration signal, the method further comprises, based on comparing a spatial relationship of the multiple detections to the known spatial relationship of the set of signal emitters, calculating an orientation of the first intelligent assistant computing device relative to the second intelligent assistant computing device.

16. The method of claim 15, where emitting the position calibration signal includes emitting at least one instance of the position calibration signal differently from other instances of the position calibration signal.

17. The method of claim 13, further comprising recording a set of parameters describing a second detection of the position calibration signal corresponding to a reflection of the position calibration signal off a reflection surface in the environment, the method further comprises, based on the set of parameters describing the second detection, estimating a relative position of the reflection surface.

18. A method, comprising:
  at a first intelligent assistant computing device, detecting presence of a human user at a first detection position within a field-of-detection (FOD) of the first intelligent assistant computing device;
  localizing the human user to a real-world position relative to an environment of the first intelligent assistant computing device corresponding to the first detection position;
  via a wireless computer network, receiving, from a second intelligent assistant computing device, an indication that the second intelligent assistant computing device detected the human user at a second detection position within a FOD of the second intelligent assistant computing device, the second detection position corresponding to the real-world position; and
  using the real-world position of the human user as a landmark, estimating real-world positions for each of the first and second intelligent assistant computing devices.

19. The method of claim 18, further comprising:
  detecting a natural language input provided by the human user;
  comparing the real-world positions of the first and second intelligent assistant computing devices to the real-world position of the human user to identify which of the first and second intelligent assistant computing devices are closer to the human user; and
  responding to the natural language input via the closer intelligent assistant computing device.

20. The method of claim 18, further comprising, upon detecting a change in position of the first intelligent assistant computing device, calculating an updated distance between the first and second intelligent assistant computing devices.

* * * * *